(12) United States Patent
Schwiegerling et al.

(10) Patent No.: US 12,383,132 B2
(45) Date of Patent: Aug. 12, 2025

(54) IDENTIFICATION AND CONTROL OF MYOPIC PROGRESSION USING DISTORTION

(71) Applicant: Arizona Board of Regents on Behalf of the University of Arizona, Tucson, AZ (US)

(72) Inventors: James T. Schwiegerling, Tucson, AZ (US); Edward Anthony Lavilla, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 884 days.

(21) Appl. No.: 17/294,344

(22) PCT Filed: Nov. 15, 2019

(86) PCT No.: PCT/US2019/061821
§ 371 (c)(1),
(2) Date: May 14, 2021

(87) PCT Pub. No.: WO2020/102734
PCT Pub. Date: May 22, 2020

(65) Prior Publication Data
US 2022/0012459 A1 Jan. 13, 2022

Related U.S. Application Data

(60) Provisional application No. 62/768,592, filed on Nov. 16, 2018.

(51) Int. Cl.
| | |
|---|---|
| *A61B 3/14* | (2006.01) |
| *A61B 3/00* | (2006.01) |
| *A61B 3/12* | (2006.01) |
| *A61B 5/00* | (2006.01) |

(Continued)

(52) U.S. Cl.
CPC ............ *A61B 3/12* (2013.01); *A61B 3/0025* (2013.01); *A61B 3/14* (2013.01); *A61B 5/4842* (2013.01); *G06V 10/145* (2022.01); *G06V 10/431* (2022.01); *G06V 40/19* (2022.01); *G06V 40/193* (2022.01); *G06V 2201/031* (2022.01)

(58) Field of Classification Search
CPC .......... A61B 3/12; A61B 3/0025; A61B 3/14; A61B 5/4842; G06V 10/145;
(Continued)

(56) References Cited

U.S. PATENT DOCUMENTS

| | | | | |
|---|---|---|---|---|
| 5,054,907 A | * | 10/1991 | Sklar ................. | G01B 11/2513 351/212 |
| 8,194,936 B2 | * | 6/2012 | Abramoff ............ | G06V 10/754 382/117 |

(Continued)

OTHER PUBLICATIONS

International Search Report and Written Opinion mailed Mar. 4, 2020, issued in International Patent Application No. PCT/US2019/061821, filed Nov. 15, 2019, 13 pages.

*Primary Examiner* — Mahidere S Sahle
(74) *Attorney, Agent, or Firm* — Barry L. Davison; Davis Wright Tremaine LLP

(57) ABSTRACT

Provided are systems (e.g., a modified fundus camera system) and methods for measuring ocular distortion, the methods comprising projecting an image of a known target pattern having characteristic features onto an area of a retinal plane/surface to provide a distorted retinal image of the target pattern across the area of the retinal surface, recording the distorted retinal image of the target pattern using an image sensor to provide a captured distorted retinal image of the target pattern across the area of the retinal surface, identifying the characteristic features of the captured distorted retinal image, and comparing the identified characteristic features of the captured distorted retinal image of the target pattern across the area of the retinal surface to (Continued)

corresponding characteristic features of the known target pattern to provide a map of ocular distortion across the area of the retinal surface. Also provided are systems and methods for measuring retinal shape.

27 Claims, 23 Drawing Sheets

(51) Int. Cl.
*G06V 10/145* (2022.01)
*G06V 10/42* (2022.01)
*G06V 40/18* (2022.01)
*G06V 40/19* (2022.01)

(58) Field of Classification Search
CPC .... G06V 10/431; G06V 40/19; G06V 40/193; G06V 2201/031
USPC .......................... 351/206, 209, 211, 221, 246
See application file for complete search history.

(56) References Cited

U.S. PATENT DOCUMENTS

| | | | |
|---|---|---|---|
| 2006/0215111 A1* | 9/2006 | Mihashi | A61B 3/103 351/205 |
| 2007/0183760 A1 | 8/2007 | Mizuno | |
| 2008/0158508 A1* | 7/2008 | Kawashima | A61B 3/14 351/206 |
| 2008/0204656 A1* | 8/2008 | Fujita | A61B 3/14 382/154 |
| 2009/0244483 A1* | 10/2009 | Yoshino | A61B 3/14 351/206 |
| 2013/0038836 A1* | 2/2013 | Smith | A61B 3/0008 351/221 |
| 2013/0063698 A1* | 3/2013 | Akiba | A61B 3/102 351/206 |
| 2016/0360963 A1 | 12/2016 | Kubota | |
| 2021/0386285 A1* | 12/2021 | Walsh | A61B 5/0066 |

* cited by examiner

| | Run 1 | Run 2 | Run 3 | Run 4 | Run 5 | Run 6 |
|---|---|---|---|---|---|---|
| Points Found Automatically | 63 | 33 | 69 | 77 | 46 | 42 |
| Spacing | 124.2 | 122.2 | 124.1 | 126.5 | 124.8 | 123.2 |

| | |
|---|---|
| Mean Spacing | 124.2 |
| STD Spacing | 1.45 |

IDENTIFICATION AND CONTROL OF MYOPIC PROGRESSION USING DISTORTION

CROSS-REFERENCE TO RELATED APPLICATIONS

This application is a 371 Nationalization of PCT International Patent Application No. PCT/US2019/061821, filed Nov. 15, 2019, which claims the benefit of U.S. Provisional Patent Application No. 62/768,592, filed Nov. 16, 2018, the disclosures of which are incorporated herein by reference in their entirety.

BACKGROUND OF THE INVENTION

Field of the Invention

The present invention relates generally to myopia and myopic progression, and more particularly to imaging systems and non-invasive methods for identification and characterization (e.g. quantifiable measurement of the amount, type and orientation of ocular distortion present in a human eye) of ocular distortion to detect the onset or progression of myopia and facilitate control of myopic progression. Additional aspects relate to methods for measuring [characterizing] retinal shape (e.g., a radius and shape, e.g., conic shape).

Description of the Related Art

Visual acuity is the measure of the human eye to perfectly resolve images from the real world onto the retina of the eye. To resolve these images in space, the main determinants of refraction (e.g., ability of the eye to bend light so that an image is focused on the retina) are the focusing power of the cornea, the crystalline lens and the length of the eye. A reduction in visual acuity from images being focused in front of the retinal plane, due to a higher curvature in the cornea or the length of the eye being too long is defined as myopia (axial myopia). When images are perfectly formed on the retina, this state is called emmetropia and an image focused behind the retinal plane is defined as hyperopia. The focusing power of the eye is often defined in units of diopters (D).

Several investigations into the optics of the human eye regarding the measurement of ocular surfaces or ocular aberrations have been conducted (Liang J, et al., "Objective measurement of wave aberrations of the human eye with the use of a Hartmann-Shack wave-front sensor," *J Opt Soc Am A.,* 11:1949-1957 (1994); Cheng, X., et al., "Relationship between refractive error and monochromatic aberrations of the eye. Optometry and Vision" *Science,* 80, 43-49 (2003); Lourdes Llorente, et al., "Myopic versus hyperopic eyes: axial length, corneal shape and optical aberrations," *Journal of Vision,* 4(4):5. doi: 10.1167/4.4.5 (2004); Susana Marcos, et al., "Investigating sources of variability of monochromatic and transverse chromatic aberrations across eyes," *Vision Research,* Volume 41, Issue 28, 3861-3871 (2001); Mathur, A., et al., "Myopia and peripheral ocular aberrations," *Journal of Vision,* 9(10):15, 1-12 (2009); Hartwig A, & Atchison DA "Analysis of higher-order aberrations in a large clinical population," *Invest Ophthalmol Vis Sci.,* 53:7862-7870 (2012), http://dx.doi.org/10.1167/iovs.12-10610; and Buehren, Tobias et al, "The Stability of Corneal Topography in the Post-Blink Interval," *Cornea.* 20. 826-33 (2001), 10.1097/00003226-200111000-00010), and have significant relevance to ocular health, quality of life, and scientific advancement. From the optical engineer's point of view, ocular aberration of the human eye is heavily influenced by the imaging optics, cornea, and crystalline lens. The predominantly studied and often corrected ocular aberrations are power error or defocus, astigmatism, coma and spherical aberration. By contrast, there has been relatively little work done in the field of optical engineering to investigate the effects of distortion, a geometrical aberration, on the human visual experience, or to investigate the related biological mechanisms. Distortion is typically ignored because traditional wavefront sensors measure aberrations at a single field point for each measurement. To measure distortion, many field points would need to be measured simultaneously.

In ophthalmology, various retinal pathologies such as macular degeneration or diabetic retinopathy require intervention or treatment after discovery. Optical coherence tomography, MRI fluorescence imaging are some techniques used to investigate the surface of the retina. Fundus photography allows for real color imaging of the retinal surface with low invasive procedural steps, and at a relatively low cost. The Amsler Grid Test provides a subjective test for patients to report deviations across a grid to potentially indicate the onset of an ailment such as macular degeneration and corneal edema.

Myopia. Myopia affects nearly one in three people in the United States and reportedly up to 80% of people in East Asian countries. When myopia moves past moderate levels (>6.00 D spherical equivalent power), serious ocular ailments can occur ranging from retinal detachment to cataracts and glaucoma. Beyond these extremes, ocular corrections related to myopia create healthcare costs in the billions and reduce the quality of life for those suffering from this condition.

Methods aimed at correcting myopia and controlling its progression are well documented. Single vision spectacle lenses, aspheric spectacle lenses, bifocal spectacle lenses, soft contact lenses, multifocal contact lenses, rigid gas permeable lenses, orthokeratology (OK) are all examples of myopic treatment and control. Some methods such as spectacle wear, try to bring distant images to the focal plane of the retina by counteracting the optical power of the cornea or overcoming an axially elongated vitreous chamber. Other methods such as OK or rigid contact lens wear try to reshape the cornea to provide the wearer with clear day vision or try to correct peripheral refraction and delay the progression of myopia. However, the long-term effectiveness of these treatments remains an open area of research and the greatest benefits of these treatments are seen at an early intervention point. However, signals that can be used to determine the onset and progression rate of myopia have not been identified.

While the exact mechanisms and their impact for onset and progression of myopia remain an active area of research, several studies point to factors such as ethnicity, age, genetics and environmental visual stimuli as some of the most predominant factors. The prevailing theory behind the progression of myopia is that the eye has a lot of astigmatism in peripheral vision. This astigmatism in turn can provide a signal to trigger eye growth. In myopia, this trigger is somehow faulty and a feedback loop is created to continuously increase eye growth leading to high levels of myopia. Various correction modalities such as contact lenses or spectacles are attempts to interfere with this astigmatism signal and disrupt the feedback loop. The mechanism is not understood and these modalities have demonstrated some effect in some patients, but fail in other patients where the progression of myopia continues and becomes more severe for the individual.

SUMMARY OF EXEMPLARY ASPECTS OF THE INVENTION

Figure 1:
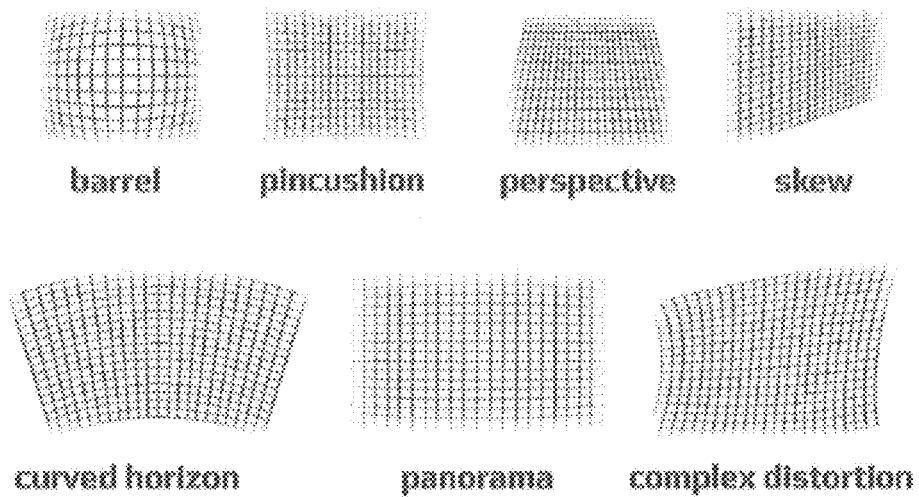
FIG. 1 shows a wide range of several possible types of distortion. Distortion creates non-uniformity and a bending of straight-line objects or rectilinear objects.

Provided is a new theory for understanding myopic onset and progression based on measuring (e.g., quantifying) distortion of an eye, and where characterization of ocular distortion provides for detecting the onset or progression of myopia. No such systems currently exist to measure the ocular distortion.

Particular aspects of the present invention provide systems and methods for measuring and quantifying distortion in the human eye as a predictor of myopia.

The systems and methods provide for quantifiable characterization of distortion in the human eye using a non-invasive imaging technique. In the methods, the amount, type and orientation of ocular distortion may be quantified, for example, using a modified fundus camera having a target pattern (e.g. grid or dot pattern) positioned in a plane of the illumination path conjugate to a retinal plane, and optimally using software extraction method(s) (e.g., image processing, variable frequency pass methods, mathematical fitting algorithms, tracking, alignment, etc.)

The systems and methods may comprise placing a target pattern in the illumination path of a fundus camera at a location that is conjugate to a retina, wherein the target pattern (e.g., grid pattern, concentric circles, arrays of dots, etc.) may comprise a known pattern that contains useful fiducials for quantifying ocular distortion.

The systems and methods may comprise placing a phase target in the illumination path of a fundus camera at a location that is a Fourier transform plane of the retina, wherein the phase target may have a suitable pattern (e.g., grid pattern, concentric circles, arrays of dots, etc.) such that its Fourier transform creates a suitable amplitude pattern on the retina for measuring ocular distortion.

The systems and methods may comprise an image sensor in the imaging path that records images of the target projected onto the retina.

The systems and methods may comprise real-time image processing software that examines features in the retinal image (e.g., blood vessels) to provide autofocus of the image and to ensure alignment of the eye between consecutive images.

The systems and methods may comprise hardware and/or software configured to track the eye (e.g., human eye) and gaze direction, ensuring eye alignment and providing useful information on eye orientation during distortion measurement.

The systems and methods may comprise software configured to analyze the captured image and automatically identify features in the target pattern. The features may then be compared to the known target pattern to quantify the amount of ocular distortion.

Additional systems and methods provide for measuring retinal shape, and may comprise software configured to enable subjects to subjectively correct a pre-distorted target and, using tracking methods, back out residual distortion and characteristics of retinal shape or asphericity from the corrected target.

Provided are methods for measuring ocular distortion present in an eye, comprising: illuminating a known target pattern having characteristic features and positioned in plane of an illumination path of a retinal imaging system that is conjugate to a retinal plane; projecting an image of the target pattern onto an area of the retinal plane to provide a distorted retinal image of the target pattern across the area of the retinal surface; projecting/focusing the distorted retinal image of the target pattern to an image sensor/detector positioned in an imaging path of the retinal imaging system; recording the distorted retinal image of the target pattern using the image sensor to provide a captured distorted retinal image of the target pattern across the area of the retinal surface; identifying the characteristic features of the captured distorted retinal image of the target pattern across the area of the retinal surface; and comparing the identified characteristic features of the captured distorted retinal image of the target pattern across the area of the retinal surface to corresponding characteristic features of the known target pattern to provide a map of ocular distortion across the area of the retinal surface.

The methods may comprise quantifying the amount of ocular distortion and/or determining the type of ocular distortion. In the methods, the retinal imaging system may comprise a fundus camera configured to include the known target pattern having the characteristic features and positioned in plane of the illumination path of the fundus camera that is conjugate to a retinal plane. In the methods, the target pattern may comprise fiducials suitable for quantifying ocular distortion, the pattern being one or more selected from the amplitude pattern group consisting of a rectilinear grid pattern, concentric ring pattern, and variable density grid pattern, or from the phase pattern group consisting of a phase plate, diffractive optic, and null correcting plate. In the methods, the target pattern may be a phase target pattern placed in the illumination path of the retinal imaging system at a location that is a Fourier transform plane of the retina, the phase target having a suitable pattern such that its Fourier transform creates a suitable amplitude pattern on the retina for measuring ocular distortion. In the methods, the amplitude pattern may comprise one or more of a grid pattern, concentric circles, or arrays of dots. In the methods, identifying the characteristic features of the captured distorted retinal image of the target pattern across the area of the retinal surface may comprise use of frequency space image processing to automatically detect centroid signatures from the target pattern. In the methods, a variable frequency pass method may be swept across the image to remove intensity variations, and suppress strong, e.g., background, objects (e.g., optic disc, blood vessels) while boosting the distorted target pattern to the foreground. In the methods, centroid or corner detection may be completed to identify various grid positions across the retinal surface. The methods may comprise quantifying the amount of ocular distortion and/or determining the type of ocular distortion using mathematical fitting. The methods may comprise correlating, using a mathematical fitting algorithm, the distorted retinal image of the target pattern across the area of the retinal surface, with the known grid pattern, free from distortion, across the area of the retinal surface. The methods may comprise calibration of the retinal imaging system for inherent distortion to provide for an absolute measurement of ocular distortion. In the methods, the retinal imaging system may be configured to distinguish between distortion caused by retinal imaging system misalignment and local changes in retinal topography, to provide for extracting a diagnostic of global and local retinal curvature. The methods may comprise or further comprise repetition of the method steps across one or more additional areas of the retinal surface to provide a map of ocular distortion across a larger retinal area/field, preferably comprising use of a stitching algorithm. The methods may comprise combining eye rotation and continuous distortion mapping. The methods may comprise or further comprise use of suitable real-time image processing software to examine features in the retinal image (e.g., blood vessels) to provide autofocus of the image and to ensure alignment of the eye between consecutive images. In the methods, the suitable retinal imaging system and software may be configured to track the human eye and gaze direction ensuring eye alignment, to provide useful information on eye orientation during distortion measurement. The methods may be applied to a subject over time (e.g., applied during critical years of eye growth) to provide a method for monitoring or tracking temporal changes or progression in distortion. The methods may comprise monitoring or tracking the change or progression in distortion relative to a distortion metric, to provide a method for detecting early onset myopia or hyperopia in patients. The methods may comprise or further comprise implementing intervention methods (e.g., corrective or control measures for ocular distortion such as spectacle lenses, contact lenses, multifocal lenses and other modalities).

Additionally provided are systems for measuring ocular distortion present in an eye, comprising: a retinal imaging system comprising an illumination system having an illumination source and an illumination path, and an imaging system having an image sensor/detector and an imaging path, wherein the illumination path is configured to project/focus light from the illumination source to a retinal plane of an eye to illuminate a retinal surface area, and wherein the imaging path is configured for projecting scattered light emerging from the illuminated retinal surface area to the image sensor/detector; and a known target pattern having characteristic features positioned and configured in a plane of the illumination path that is conjugate to the retinal plane, such that upon illumination an image of the known target pattern is projectable onto the retinal surface area to provide for a distorted retinal image of the target pattern across the area of the retinal surface, and wherein the image sensor is configured for recording of the distorted retinal image of the target pattern across the area of the retinal surface. The systems may comprise or further comprise computer implemented software for identifying the characteristic features of the captured distorted retinal image of the target pattern across the area of the retinal surface, and comparing the identified characteristic features of the captured distorted retinal image of the target pattern across the area of the retinal surface to corresponding characteristic features of the known target pattern to provide a map of ocular distortion across the area of the retinal surface. The systems may comprise or further comprise computer implemented software for real-time image processing of features in the retinal image (e.g., blood vessels) to provide for autofocus of the image and for eye alignment between consecutive images. In the systems, the retinal imaging system and software may be configured to track the eye and gaze direction to provide for eye alignment, to provide useful information on eye orientation during distortion measurement. In the systems, the target pattern may comprise fiducials suitable for quantifying ocular distortion, the pattern being at least one selected from the amplitude pattern group consisting of, e.g., a rectilinear grid pattern, concentric ring pattern, and variable density grid pattern, or from the phase pattern group consisting of a phase plate, diffractive optic, and/or null correcting plate. In the systems, the target pattern may be a phase target pattern placed in the illumination path of the retinal imaging system at a location that is a Fourier transform plane of the retina, the phase target having a suitable pattern such that its Fourier transform creates a suitable amplitude pattern on the retina for measuring ocular distortion. In the systems, the amplitude pattern may comprise, e.g., one or more of a grid pattern, concentric circles, or arrays of dots, etc. In the systems, the retinal imaging system may comprises a fundus camera.

Further provided are methods for measuring retinal shape, comprising: displaying, to a subject, an image of a known distorted target pattern having characteristic features and characterized in terms of size and shape relative to the distance away from the subject's eye; tracking the edge points of the distorted target pattern during correction or un-distortion of the distorted target pattern by the subject, until the characteristic features are undistorted to provide a baseline measure for the amount of distortion present in the subject's eye; placing a lens of a given power in front of the subject's eye; tracking the edge points of the distorted target pattern during correction or un-distortion of the distorted target pattern by the subject, until the characteristic features are undistorted to provide a measure for the amount of distortion present in the subject's eye; and determining, using the baseline measure and the lens measure, a radius and/or shape (e.g., conic shape) of the subject's retina (based on the presumption that the amount of distortion changes equivalently for a given retinal shape). In the methods, the distorted target pattern may comprises a grid pattern having distorted lines, and wherein correction or un-distortion of the distorted target pattern by the subject may comprise correcting or un-distorting the distorted grid lines of the grid until they are straight and square. In the methods, correction or un-distortion of the distorted target pattern by the subject and tracking thereof to determine residual distortion and characteristics of retinal shape or asphericity from the corrected target may comprise use of suitable software (e.g., image processing, mathematical fitting algorithms, tracking, alignment, etc.).

Embodiments of the disclosure can be described in view of the following clauses:

1. A method for measuring ocular distortion present in an eye, comprising: illuminating a known target pattern having characteristic features and positioned in plane of an illumination path of a retinal imaging system that is conjugate to a retinal plane;

projecting an image of the target pattern onto an area of the retinal plane to provide a distorted retinal image of the target pattern across the area of the retinal surface;

projecting the distorted retinal image of the target pattern to an image sensor positioned in an imaging path of the retinal imaging system;

recording the distorted retinal image of the target pattern using the image sensor to provide a captured distorted retinal image of the target pattern across the area of the retinal surface;

identifying the characteristic features of the captured distorted retinal image of the target pattern across the area of the retinal surface; and comparing the identified characteristic features of the captured distorted retinal image of the target pattern across the area of the retinal surface to corresponding characteristic features of the known target pattern to provide a map of ocular distortion across the area of the retinal surface.

2. The method of clause 1, comprising quantifying the amount of ocular distortion and/or determining the type of ocular distortion.

3. The method of clause 1 or 2, wherein the retinal imaging system comprises a fundus camera configured to include the known target pattern having the characteristic features and positioned in plane of the illumination path of the fundus camera that is conjugate to a retinal plane.

4. The method of any one of clauses 1-3, wherein the target pattern comprises fiducials suitable for quantifying ocular distortion, the pattern being one or more selected from the amplitude pattern group consisting of a rectilinear grid pattern, concentric ring pattern, and variable density grid pattern, or from the phase pattern group consisting of a phase plate, diffractive optic, and null correcting plate.

5. The method of any one of clauses 1-4, wherein the target pattern is a phase target pattern placed in the illumination path of the retinal imaging system at a location that is a Fourier transform plane of the retina, the phase target having a suitable pattern such that its Fourier transform creates a suitable amplitude pattern on the retina for measuring ocular distortion.

6. The method of clause 5, wherein the amplitude pattern comprises one or more of a grid pattern, concentric circles, or arrays of dots.

7. The method of any one of clauses 1-6, wherein identifying the characteristic features of the captured distorted retinal image of the target pattern across the area of the retinal surface, comprises use of frequency space image processing to automatically detect centroid signatures from the target pattern.

8. The method of clause 7, wherein a variable frequency pass method is swept across the image to remove intensity variations, and suppress strong objects (e.g., optic disc, blood vessels) while boosting the distorted target pattern to the foreground.

9. The method of clause 8, wherein centroid or corner detection is completed to identify various grid positions across the retinal surface.

10. The method of any one of clauses 1-9, comprising quantifying the amount of ocular distortion and/or determining the type of ocular distortion using mathematical fitting.

11. The method of clause 10, comprising correlating, using a mathematical fitting algorithm, the distorted retinal image of the target pattern across the area of the retinal surface, with the known grid pattern, free from distortion, across the area of the retinal surface.

12. The method of clause 11, comprising calibration of the retinal imaging system for inherent distortion to provide for an absolute measurement of ocular distortion.

13. The method of any one of clauses 1-12, wherein the retinal imaging system is configured to distinguish between distortion caused by retinal imaging system misalignment and local changes in retinal topography, to provide for extracting a diagnostic of global and local retinal curvature.

14. The method of any one of clauses 1-13, further comprising repetition of the method steps across one or more additional areas of the retinal surface to provide a map of ocular distortion across a larger retinal area, preferably comprising use of a stitching algorithm.

15. The method of clause 14, comprising combining eye rotation and continuous distortion mapping.

16. The method of any one of clauses 1-15, further comprising use of suitable real-time image processing software to examine features in the retinal image (e.g., blood vessels) to provide autofocus of the image and to ensure alignment of the eye between consecutive images.

17. The method of clause 16, wherein the retinal imaging system and software are configured to track the human eye and gaze direction ensuring eye alignment, to provide useful information on eye orientation during distortion measurement.

18. The method of any one of clauses 1-17, applied to a subject over time, to provide a method for monitoring or tracking temporal changes or progression in distortion.

19. The method of clause 18, applied during critical years of eye growth.

20. The method of clause 18 or 19, comprising monitoring or tracking the change or progression in distortion relative to a distortion metric, to provide a method for detecting early onset myopia or hyperopia in patients.

21. The method of clause 20, further comprising implementing intervention methods (e.g., corrective or control measures for ocular distortion such as spectacle lenses, contact lenses, multifocal lenses and other modalities).

22. A system for measuring ocular distortion present in an eye, comprising:

a retinal imaging system comprising an illumination system having an illumination source and an illumination path, and an imaging system having an image sensor and an imaging path, wherein the illumination path is configured to project light from the illumination source to a retinal plane of an eye to illuminate a retinal surface area, and wherein the imaging path is configured for projecting scattered light emerging from the illuminated retinal surface area to the image sensor; and a known target pattern having characteristic features positioned and configured in a plane of the illumination path that is conjugate to the retinal plane, such that upon illumination an image of the known target pattern is projectable onto the retinal surface area to provide for a distorted retinal image of the target pattern across the area of the retinal surface, and wherein the image sensor is configured for recording of the distorted retinal image of the target pattern across the area of the retinal surface.

23. The system of clause 22, further comprising computer implemented software for identifying the characteristic features of the captured distorted retinal image of the target pattern across the area of the retinal surface, and comparing the identified characteristic features of the captured distorted retinal image of the target pattern across the area of the retinal surface to corresponding characteristic features of the known target pattern to provide a map of ocular distortion across the area of the retinal surface.

24. The system of clauses 22 or 23, further comprising computer implemented software for real-time image processing of features in the retinal image (e.g., blood vessels) to provide for autofocus of the image and for eye alignment between consecutive images.

25. The system of clause 24, wherein the retinal imaging system and software are configured to track the eye and gaze direction to provide for eye alignment, to provide useful information on eye orientation during distortion measurement.

26. The system of any one of clauses 22-25, wherein the target pattern comprises fiducials suitable for quantifying ocular distortion, the pattern being one or more selected from the amplitude pattern group consisting of a rectilinear grid pattern, concentric ring pattern, and variable density grid pattern, or from the phase pattern group consisting of a phase plate, diffractive optic, and null correcting plate.

27. The system of any one of clauses 22-26, wherein the target pattern is a phase target pattern placed in the illumination path of the retinal imaging system at a location that is a Fourier transform plane of the retina, the phase target having a suitable pattern such that its Fourier transform creates a suitable amplitude pattern on the retina for measuring ocular distortion.

28. The system of clause 26, wherein the amplitude pattern comprises one or more of a grid pattern, concentric circles, or arrays of dots.

29. The system of any one of clause 22-28, wherein the retinal imaging system comprises a fundus camera.

30. A method for measuring retinal shape, comprising:
displaying, to a subject, an image of a known distorted target pattern having characteristic features and characterized in terms of size and shape relative to the distance away from the subject's eye;
tracking the edge points of the distorted target pattern during correction or un-distortion of the distorted target pattern by the subject, until the characteristic features are undistorted to provide a baseline measure for the amount of distortion present in the subject's eye;
placing a lens of a given power in front of the subject's eye;
tracking the edge points of the distorted target pattern during correction or un-distortion of the distorted target pattern by the subject, until the characteristic features are undistorted to provide a measure for the amount of distortion present in the subject's eye; and
determining, using the baseline measure and the lens measure, a radius and/or shape (e.g., conic shape) of the subject's retina (e.g., based on the presumption that the amount of distortion changes equivalently for a given retinal shape).

31. The method of clause 30, wherein the distorted target pattern comprises a grid pattern having distorted lines, and wherein correction or un-distortion of the distorted target pattern by the subject comprises correcting or un-distorting the distorted grid lines of the grid until they are straight and square.

32. The method of clause 30 or 31, wherein correction or un-distortion of the distorted target pattern by the subject and tracking thereof to determine residual distortion and characteristics of retinal shape or asphericity from the corrected target comprises use of suitable software (e.g., image processing, mathematical fitting algorithms, tracking, alignment, etc.).

DETAILED DESCRIPTION OF THE INVENTION

According to particular aspects of the invention, distortion, rather than astigmatism, is a primary trigger for onset and progression of myopia, and systems and methods for measuring distortion in the eye and lens corrections that affect the eye's distortion are provided.

Figure 27:
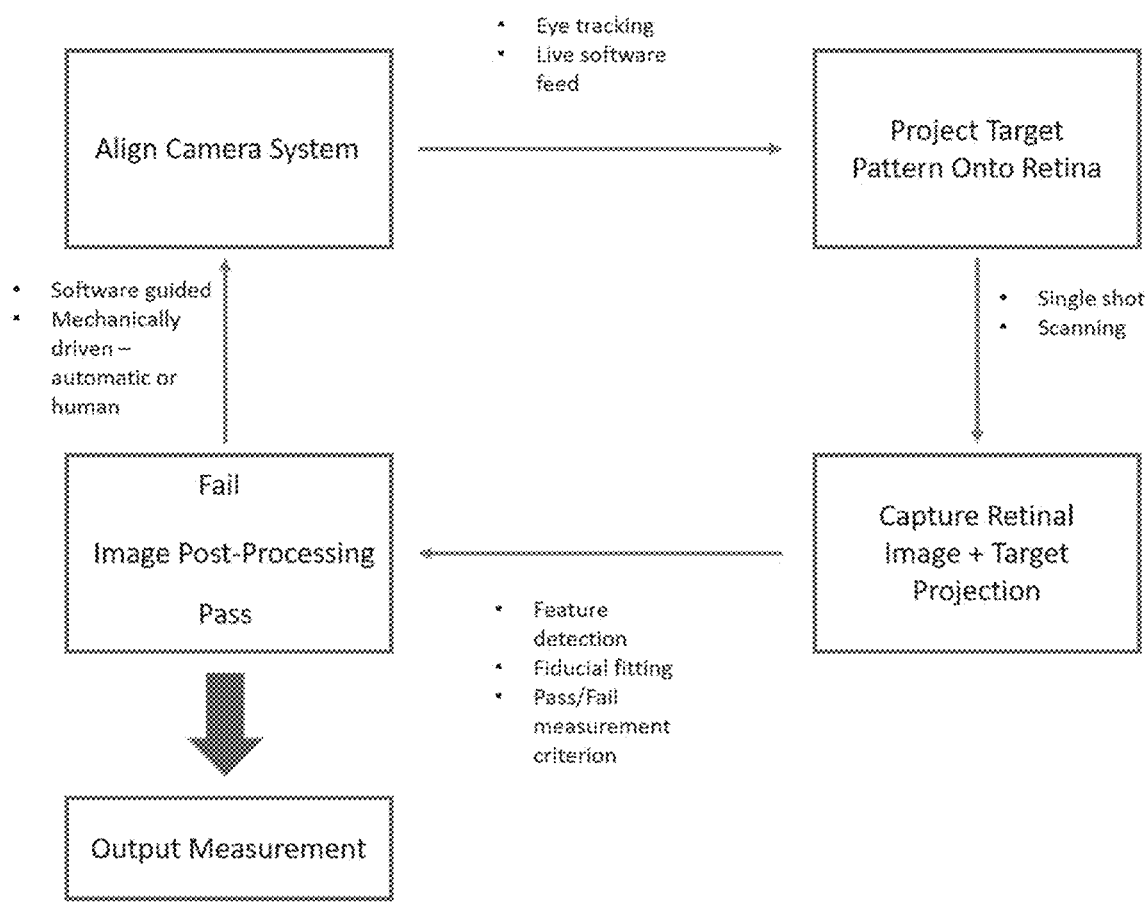
FIG. 27 shows a summary of three basic functions relating to measurement of ocular distortion according to particular exemplary aspects of the present invention. First, a known target pattern is projected onto the retinal surface. Second, an image sensor captures the image of the target on the retinal surface. Third, post processing of target fiducials back out useful information related to ocular distortion.

FIG. 27 shows a schematic summary of three basic functions relating to measurement of ocular distortion according to particular exemplary aspects of the present invention. First, a known target pattern is projected onto the retinal surface. Second, an image sensor captures the image of the target on the retinal surface. Third, post processing of target fiducials back out useful information related to ocular distortion.

Particular aspects provide systems and methods for measuring distortion in the eye as a predictor of myopia, and lens corrections that affect the eye's distortion are provided.

Exemplary systems include, but are not limited to measuring devices comprising, for example, an adaptation to a traditional fundus camera system, or scanning methods, for the purpose of measuring or detecting distortion in the human eye.

Exemplary systems (e.g., a modified fundus camera system) and methods for measuring ocular distortion comprise projecting an image of a known target pattern having characteristic features onto an area of a retinal plane/surface to provide a distorted retinal image of the target pattern across the area of the retinal surface, recording the distorted retinal image of the target pattern using an image sensor to provide a captured distorted retinal image of the target pattern across the area of the retinal surface, identifying the characteristic features of the captured distorted retinal image, and comparing the identified characteristic features of the captured distorted retinal image of the target pattern across the area of the retinal surface to corresponding characteristic features of the known target pattern to provide a map of ocular distortion across the area of the retinal surface.

Additional aspects provide methods for measuring retinal shape.

Distortion

There are several types of distortion that are possible. FIG. 1 shows a wide range of these various types of distortion. Distortion creates non-uniformity and a bending of straight-line objects or rectilinear objects. In traditional optical systems, distortion can be introduced by decentering or misaligning lens elements, tilting a detection plane or through manufacturing defects of lens elements. Furthermore, distortion is highly dependent on field of view and orientation, where imaging systems with a wide field of view traditionally exhibit high amounts of distortion.

According to particular aspects of the present invention, the human eye may experience a high amount of distortion that is corrected, at least to some degree by the brain. Characterizing the amount and type of distortion present in the human eye has not been done before and, prior to Applicant's present disclosure, remained an unexplored topic with respect to its effect on eye growth and development.

Particular aspects of the present invention provide a method for measuring absolute distortion in the human eye as a new diagnostic tool. The methods provide, for example, for understanding and characterization of normal eye growth in pediatric subjects, determining the onset or progression of myopia, as well as a characterization method for retinal shape.

Particular aspects provide a measuring device comprising an adaptation to a traditional fundus camera system for the purpose of measuring or detecting distortion in the human eye.

Systems

According to particular aspects of the invention, various optical configurations (hardware/software) can be constructed to perform ocular distortion measurement. A modified fundus camera configuration for measuring ocular distortion is one such example of a hardware/software solution to this problem.

Figure 2:
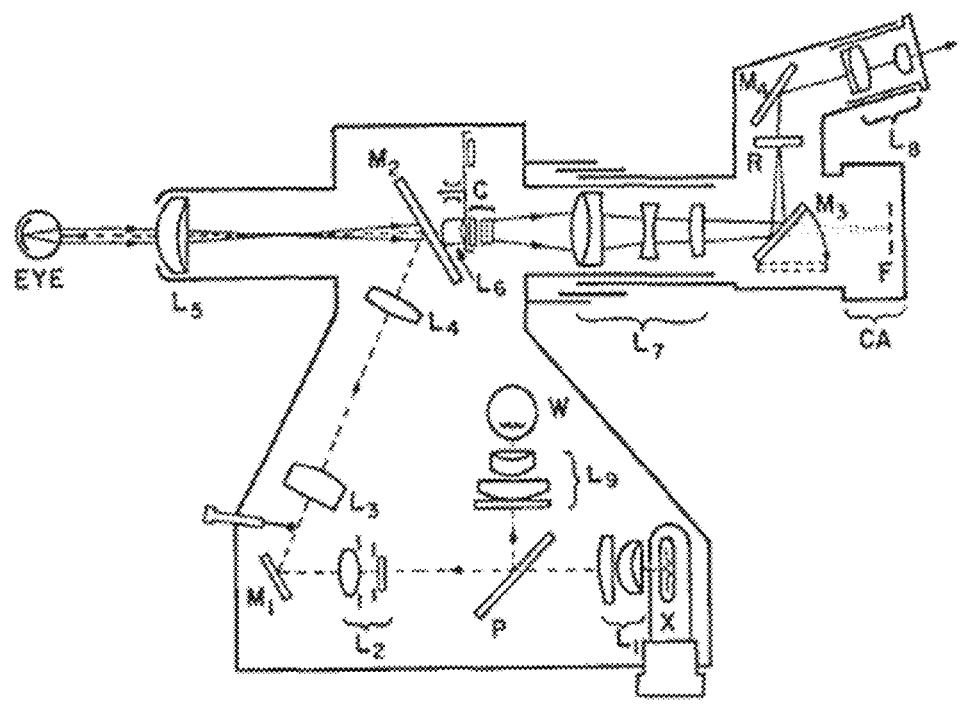
FIG. 2 shows a schematic of a traditional fundus camera system from Zeiss (reproduced from Wiggins et al., *Applied Optics* 1:179-181 (1972).

A fundus camera allows the operator to image the retina directly. Most fundus camera design requirements and documentation is found In patent literature (see, e.g., N. Shibata, and M. Torii, "Fundus Camera," U.S. Pat. No. 6,654,553 (2003); N. Shibata, "Fundus Camera," U.S. Pat. No. 6,755,526 (2004); N. Kishida and S. Ono, "Eye Fundus Examination Apparatus," U.S. Pat. No. 7,055,955 (2006); N. Ichikawa, "Fundus Camera," U.S. Pat. No. 7,219,996 (2007); K. Matsumoto, "Fundus Image-Taking Apparatus and Method," U.S. Pat. No. 6,832,835 (2004); T. Nanjo and M. Kawamura, "Fundus Camera," U.S. Pat. No. 574,274 (1998); Y. Sugina, T. Abe, T. Takeda and T. Kogawa, "Ophthalmologic Photographing Apparatus," U.S. Pat. No. 7,147,328 (2004); Filipp V. Ignatovich, et al., "Portable Fundus Camera," U.S. Pat. No. 8,836,778 (2014); Paul Andrew Yates, Kenneth Tran, "Hand-held portable fundus camera for screening photography," PCT Patent Application WO2011/029064). FIG. 2 illustrates a schematic of a traditional fundus camera system from Zeiss.

A fundus camera consists of three main systems, which are an illumination system, an imaging system and fixation target that all share a common optical path. The illumination system consists of one or more sources (see, e.g., X and W in FIG. 2) with a series of condensing optics (L9 and L1 in FIG. 2). Light travels through a glass plate P, to a field lens and aperture L2 before being directed up to a relay system by mirror M1. Camera lenses L3 and L4 project light onto the surface of mirror M2 which has a hole in it. This hole is projected into the plane of the pupil in the eye by an aspheric objective lens L5. The light is then focused to the retinal plane of the eye to illuminate the retinal surface. Light scattered from the retinal surface emerges from the eye, back into the camera system again through L5, projecting the image of the retina through the hole in M2. Lenses L6 and C combine with lens system L7 to relay the retinal image to a detector F or a monocular viewing plane at the end of lens system Lb. Lens system L7 is a reverse telephoto system that provides correction to any ocular aberration in the form of defocus.

According to particular aspects of the present invention, the prior art system detailed in FIG. 2 is modified by placing a known pattern, capable of picking up distortion of the eye, in a plane between mirror M1 and lens L3 that is conjugate to the retina. This element may be, but is not limited to, at least one element selected from the group consisting of a rectilinear grid pattern, concentric ring pattern(s), a variable density grid pattern, phase plate, diffractive optic, and/or null correcting plate.

Alternatively, scanning systems can be constructed to perform ocular distortion measurement, wherein a beam is scanned over the surface of the retina in a raster pattern. Modulation of the beam at certain positions in the scanning cycle provides for measurement of ocular distortion. For example, the beam may be turned off when scanning over known grid positions and back on for regions not on the grid, and the resulting raster image will appear to have the projected target superimposed on the retinal surface. Such a scanning method creates the known grid pattern point by point during the scan and records the deviation of each point on the retina to build the ocular distortion map.

Method for Measuring the Amount and Type of Distortion

Figure 3:
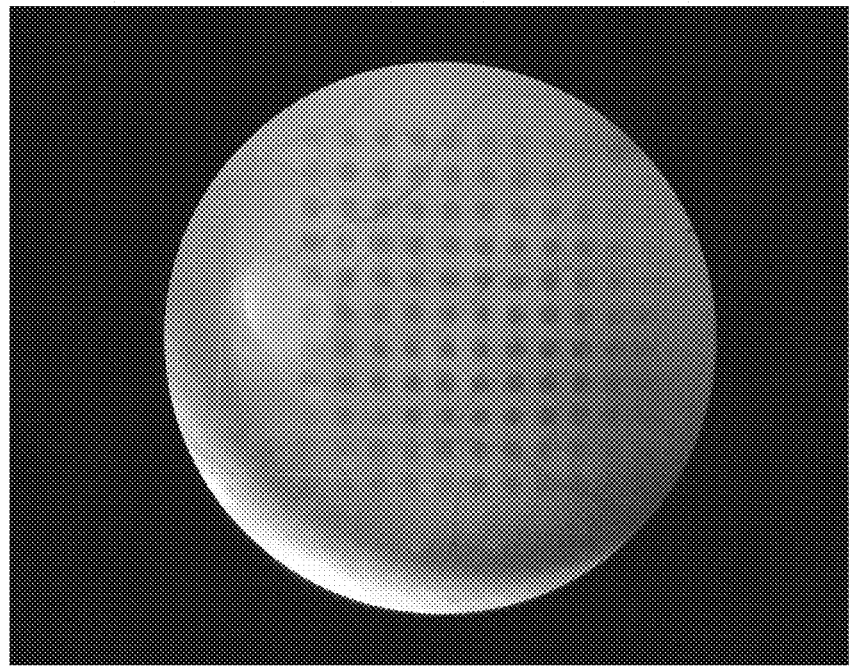
FIG. 3 shows, according to particular exemplary aspects of the present invention, a wire grating projected onto a human retina and imaged using a modified fundus camera as disclosed and described herein.

According to additional aspects, imaging the proposed pattern onto the retina and post processing the detector image provides for revealing the amount and type of distortion present in the eye. FIG. 3 shows, according to an exemplary embodiment, considerable complex distortion shown after grid projection into a human eye. Specifically, in FIG. 3, a transparent plate with a rectangular grid of dots was placed at the location between M1 and L3 (with reference to FIG. 2), and the illumination system effectively projected this grid pattern onto the retina. The image of FIG. 3 was captured through a custom mount used to couple an eyepiece imaging path L8 (with reference to FIG. 2) to a camera cellphone for high resolution imaging. In further exemplary embodiments, such images were captured with a digital camera placed at location F of FIG. 2. FIG. 3 shows the optic nerve (light gray oval in the left of the image), retinal blood vessels and the dot pattern projected onto the retinal surface. Multiple people have been imaged in a similar manner and a variation between eyes of various refractive error, age, ethnicity, and gender have been observed.

Figure 4:
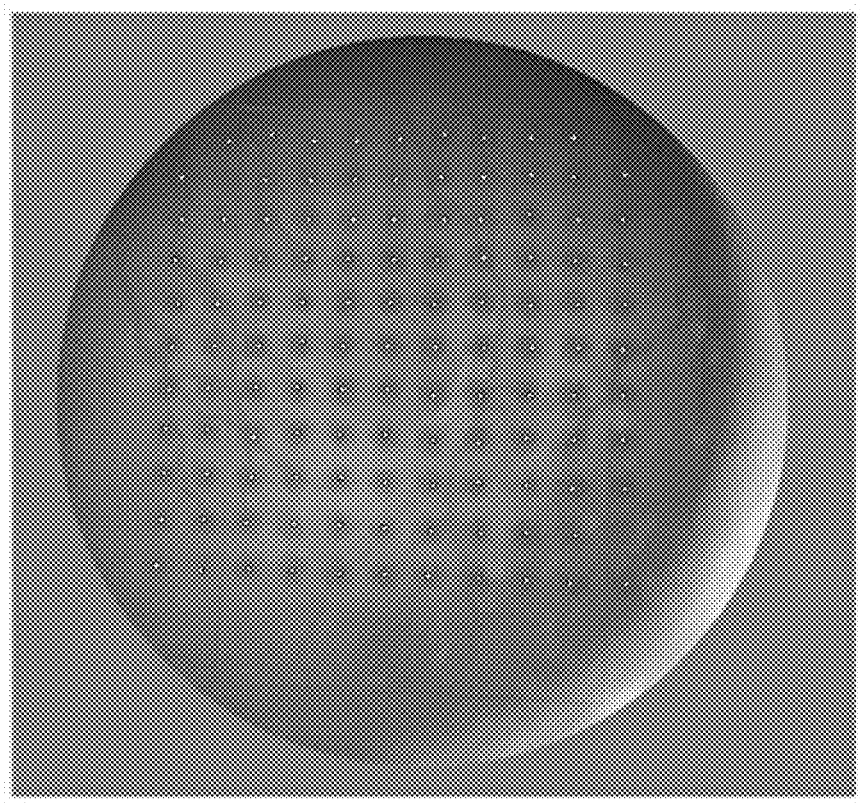
FIG. 4 shows, according to particular exemplary aspects of the present invention, distortion pattern detection using a point extraction software package.

Additional aspects provide a method (e.g., using a software package) to extract the amount and type of ocular distortion present in the human eye. A detection of centroid signatures from the grid pattern are found automatically from frequency space image processing. A variable frequency pass method is swept across the image to remove intensity variations, suppress strong objects such as the optic disc and blood vessels while boosting the distortion pattern to the foreground. From here, centroid or corner detection is completed to identify various grid positions across the retinal surface. With knowledge of the grid target pattern a calculation of absolute distortion can be completed through mathematical fitting. FIG. 4 shows distortion pattern detection using the method implemented with the point extraction software package.

Figure 5:
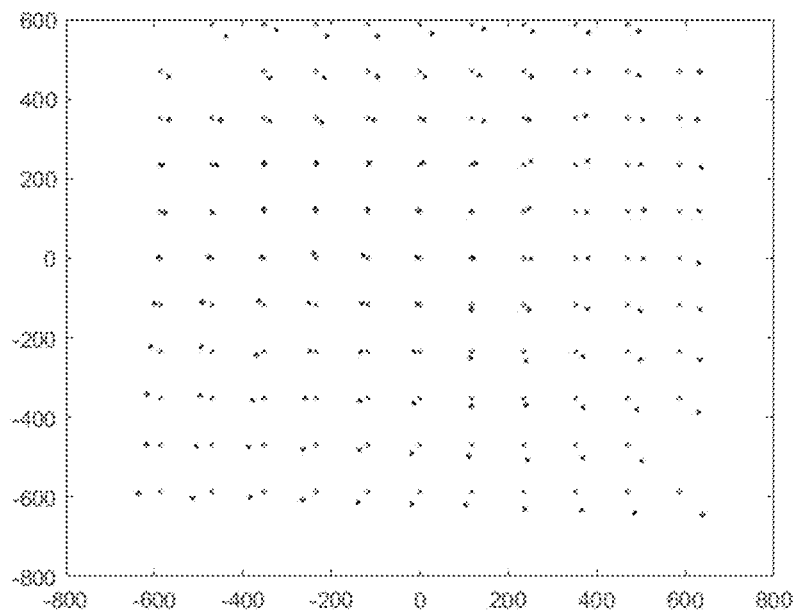
FIG. 5 shows, according to particular exemplary aspects of the present invention, an ocular distortion map. The undistorted grid is shown in gray with the ocular distortion pattern shown in black.

To quantify the amount and type of distortion for each measured eye, a mathematical fitting algorithm was developed that correlates an optimal grid pattern on the retina, free from distortion, with the experimental distortion results. Calibration of the camera system for inherent distortion allows for an absolutely measurement of ocular distortion. From this point, a map of ocular distortion across the retinal surface can be produced as seen in FIG. 5 where the red dots represent the undistorted pattern and the black dots are the ocular distortion pattern.

According to further aspects, the camera system distinguishes between distortion caused by camera misalignment (e.g., strong keystone effect) and distortion when aligned (e.g., local changes in retinal topography). The reduction of this distortion noise allows the diagnostic of global and local retinal curvature to be extracted. Furthermore, combining eye rotation and continuous distortion mapping, a larger area and field of retinal topography can be mapped and measured by using a stitching algorithm for several images.

The system and methods provide a means of objectively measuring distortion in the eye, as well as monitoring temporal changes in distortion. Implementing this device and method into regular checkups for young children, for example, provides for the tracking of ocular distortion changes during critical years of eye growth. According to yet further aspects, therefore, watching the change or progression in the context of a distortion metric provides for detecting early onset myopia or hyperopia in patients, and further provides for implementing intervention methods, e.g., corrective or control measures for ocular distortion such as spectacle lenses, contact lenses, multifocal lenses, and other modalities.

Method for Measuring Retinal Shape

Yet additional aspects provide a method for measuring retinal shape. With knowledge of the anterior and posterior corneal radii of curvature, the corneal thickness, the axial length of the eye, the anterior and posterior crystalline lens radii of curvature, and the crystalline lens thickness, it is possible to determine the retinal radius of curvature and conic shape.

The method comprises displaying, to a subject, a known grid pattern in terms of size and shape relative to the distance away from a subject's eye. The subject is asked to correct or un-distort the image such that the lines of the grid are straight and square. Tracking the edge points of the grid during this process provides the baseline for the amount of distortion present in the subject's eye.

Figure 6:
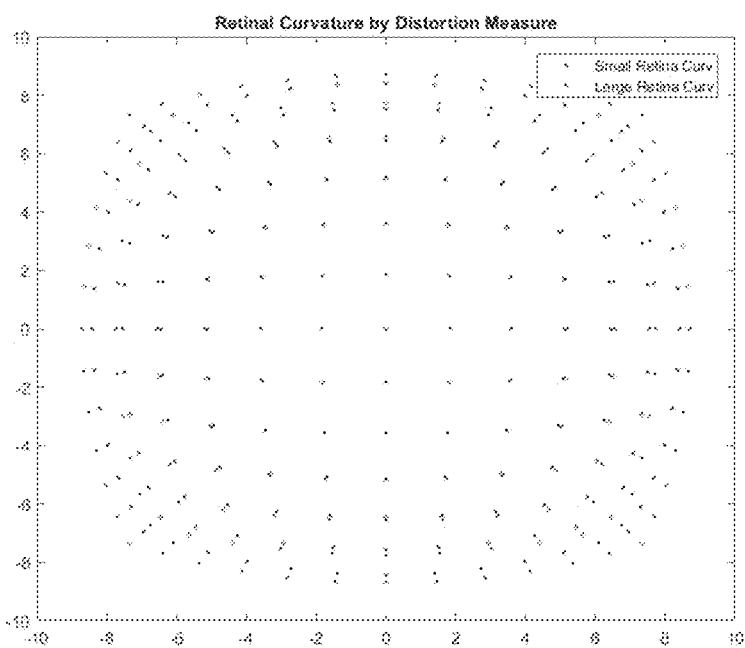
FIG. 6 shows, according to particular exemplary aspects of the present invention, comparison of distortion between small and large retinal curvatures

Next, a lens of a given power is placed in front on the subject's eye. Again with a known grid pattern, the subject is asked to un-distort the grid pattern and the changes are tracked. For any given eye in the human population, the amount of distortion changes equivalently for a given retinal shape. Thus, information from the baseline and lens case can be used to back out the retinal radius and conic shape. FIG. 6, shows, according to particular exemplary aspects of the present invention, comparison of distortion between small and large retinal curvatures.

Example 1

A Target Pattern was Placed in the Illumination Path of a Fundus Camera at a Location that is Conjugate to a Retina This exemplary working example describes placing a target pattern in the illumination path of a modified fundus camera at a location that is conjugate to a retina.

Figure 7:
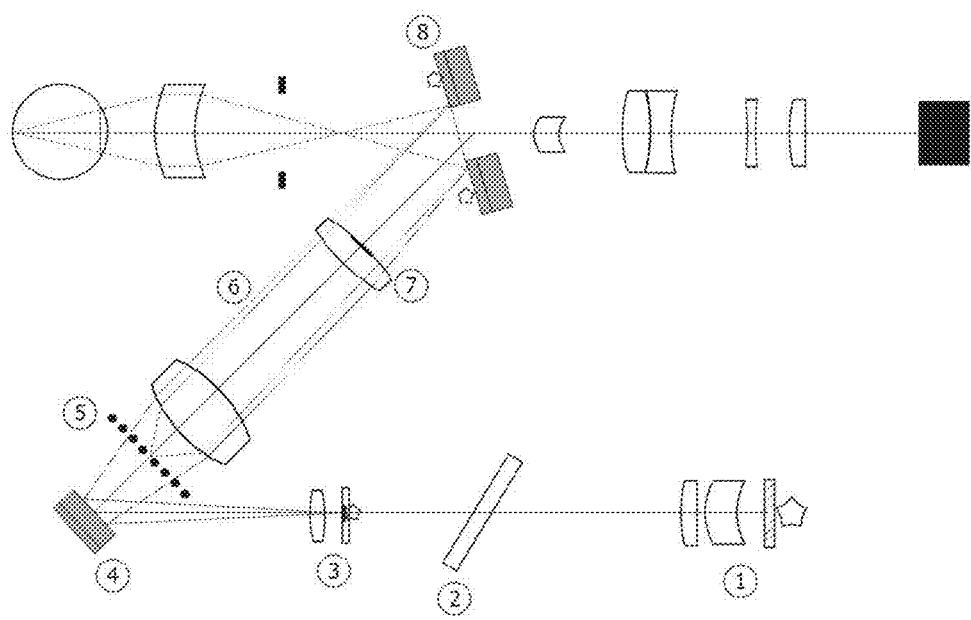
FIG. 7 shows, according to particular exemplary aspects of the present invention, a source image and annulus mask at location 3 that are conjugate to the holed mirror at location 8. The dot grid pattern at location 5 is picked up along the illumination path and is conjugate to the retina by the holed mirror.

FIG. 7 shows a source image and annulus mask at location 3 that are conjugate to a holed mirror at location 8. The dot grid pattern at location 5 is picked up along the illumination path and is conjugate to the retina by the holed mirror (red). A series of aspheric condensing lenses compress and image the illumination through a glass plate at location 2 to an intermediate image plane at location 3, where a set of adjustable apertures lie. There is a second opening located above the glass plate where a second source can be placed in the illumination path. Given that the fundus camera uses an internal illumination scheme, the critical annulus used to eliminate corneal back reflections is placed at location 3 where the intermediate source image is formed. A first modification to the fundus camera may be replacing, e.g., a 60 W incandescent bulb source with three 1 W LED's from CREE at location 1 to provide equivalent light throughput for illuminating the retinal surface. A piece of ground glass may be placed in front of the LED suite to create a diffuse light source.

As illustrated in FIG. 7, the second arm of the illumination pathway of the modified fundus camera creates an intermediate image of the source and annulus at a conjugate plane with a holed mirror seen at location 8. After a being redirected by a fold mirror at location 4, a second modification to the fundus camera, a grid pattern for measuring ocular distortion, is picked up by the illumination path at location 5. The grid pattern at location 5 is conjugate to the retinal surface, or equivalently, the location of the intermediate image of the retina, which forms before the holed mirror at location 5 and is shown in red. The legacy (prior art) system has a small fixation target located at the same location as plane 5 which was used to fix a subject's gaze during measurement and served as the intended target plane location. Objective elements at location 6 complete the relay path to the holed mirror. There is a central black dot obscuration at location 7 that is conjugate to the back surface of the aspheric objective lens. The obscuration eliminates the back reflections from the two objective surfaces from entering the imaging path.

Figure 8:
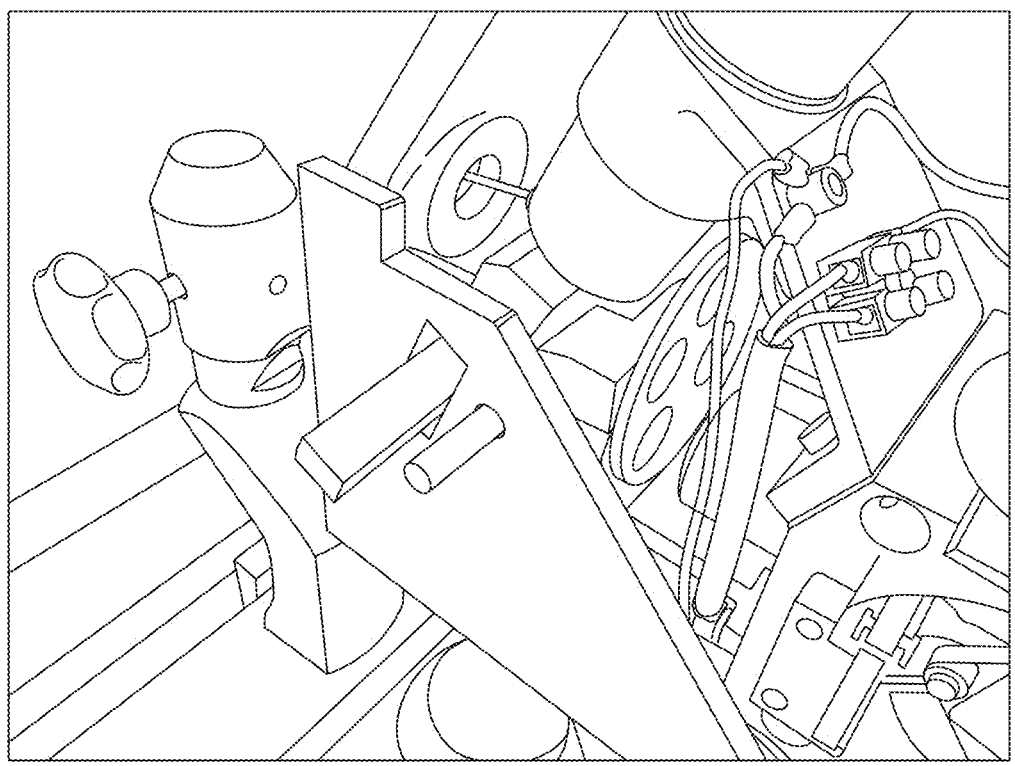
FIG. 8 shows, according to particular exemplary aspects of the present invention, a 3D printed cover and grid target holder. The grid target, fixed to a glass plate, is placed conjugate to the intermediate retina.

The grid target used in this exemplary body of work was chosen to be a rectilinear grid of dots with a diameter of 0.5 mm and spacing of 1 mm. The actual dot diameter and spacing was measured on a Zygo NewView 8300 interferometer, used primarily as a microscope in this case. The true dot diameter is approximately 0.642 mm and spacing of 1 mm. A piece of glass supported the grid target and both were fixed to a 3D printed mount. The mount arm fixed to the existing body of the fundus camera through a set of three screws and was fixed in place at location 5. The target was aligned using a model eye on an optical bench and the Z location corresponding to the distance away from the fold mirror at location 4 was determined by imaging an emmetropic subject and finding the plane of best focus for the grid pattern. FIG. 8 shows the mounting scheme for the grid target; a 3D printed cover and grid target holder. The grid target, fixed to a glass plate, is located inside the red circle of the image and placed conjugate to the intermediate retina.

Figure 9:
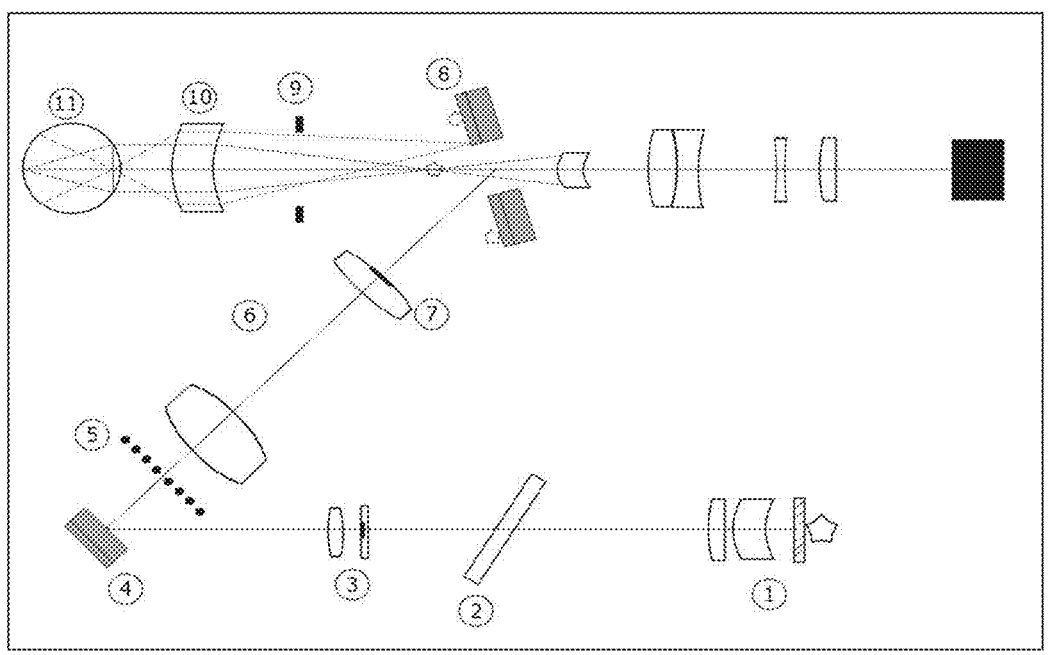
FIG. 9 shows, according to particular exemplary aspects of the present invention, the retinal illumination and return path of the modified fundus camera. The holed mirror image at location 8 is conjugate to the pupil of the eye located at 11. An intermediate image of the retina with the grid target projection becomes the object presented to the imaging pathway for detection.
Figure 10:
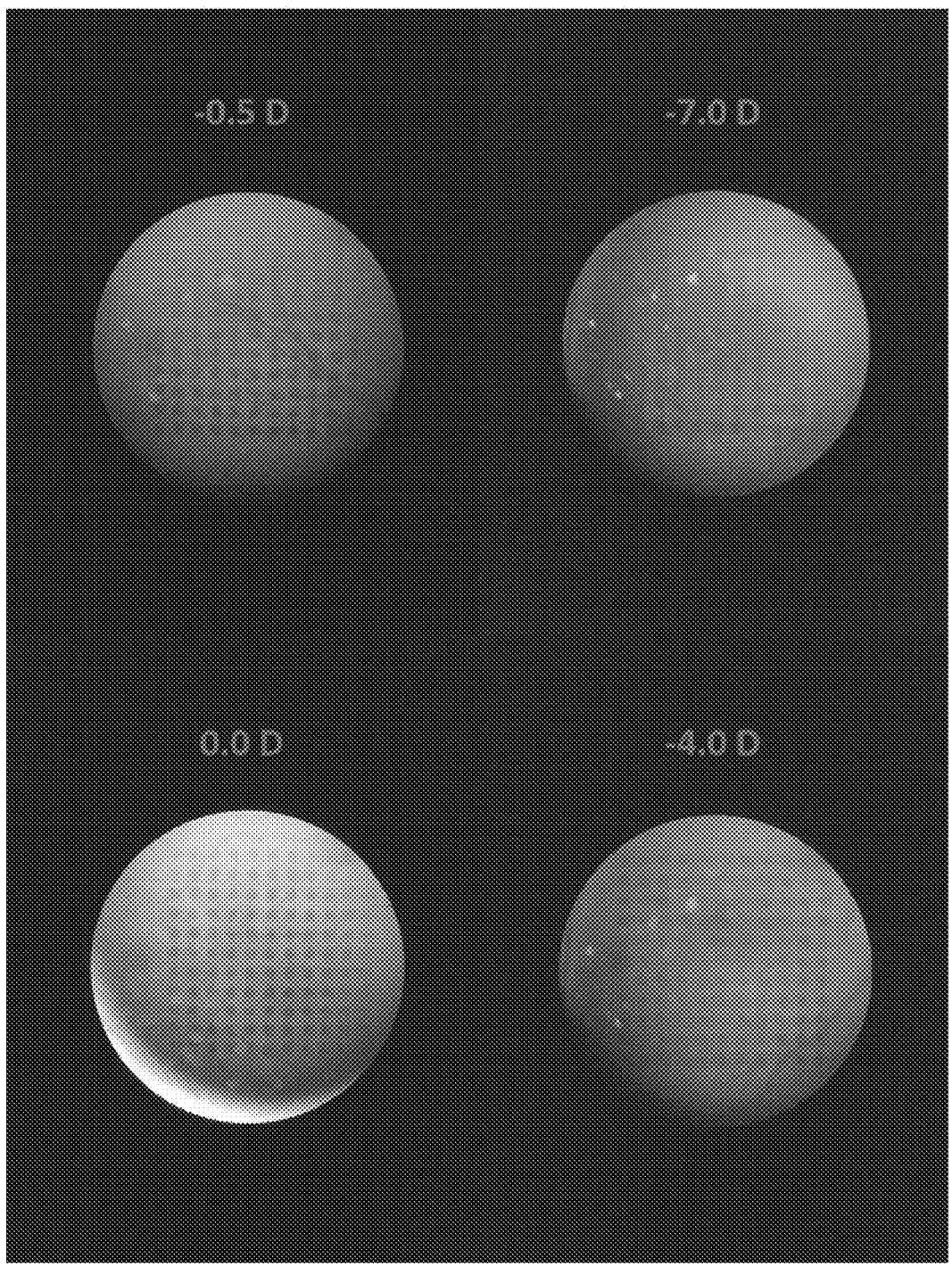
FIG. 10 shows, according to particular exemplary aspects of the present invention, four retinal images with the projected grid pattern from cohort subjects. Self-reported refractive error is listed above each image.

FIG. 9 illustrates, according to particular exemplary aspects of the present invention, the retinal illumination and return path of the modified fundus camera. The holed mirror image at location 8 is conjugate to the pupil of the eye located at 11. An intermediate image of the retina with the grid target projection becomes the object presented to the imaging pathway for detection (red). The grid pattern projection onto the retina is accomplished by making the holed mirror conjugate to the pupil plane of the eye at location 11. A baffle at location 9 helps to further control the corneal back reflections returned into the imaging path way. The aspheric objective lens at location 11 serves a critical role in the fundus camera design. A fast objective, approximately f/2 is responsible for bringing the annulus of light into focus at the pupil of the eye. A uniform illumination covers the retinal surface and effectively creates a virtual object of the retina and grid pattern at infinity to be recorded by the imaging pathway (133).

The retinal surface can be considered a Lambertian scatterer (134) that has different reflectance values for wavelengths in the visual band, with red light having the highest value around 40% (135). Thus, a strong illumination source is required to have sufficient intensity of the retinal image compared to return signals from unwanted surfaces such as the anterior cornea. The light exiting the eye is telecentric passing into the aspheric objective. Here the objective must flatten the curvature of the retina to ensure plane to plane imaging. Pomerantzeff, et. al., illustrates the difficulty in flattening the curvature of the retina for large angles to a common flat focus plane (133). Therefore, careful attention to the optical design of such an objective as well as additional lens components may be used to further improve to the legacy fundus imaging system.

FIGS. 10-14 show, according to particular exemplary aspects of the present invention, seventeen (17) retinal images with the projected grid pattern from cohort subjects. Self-reported refractive error is listed above each image.

Figure 11:
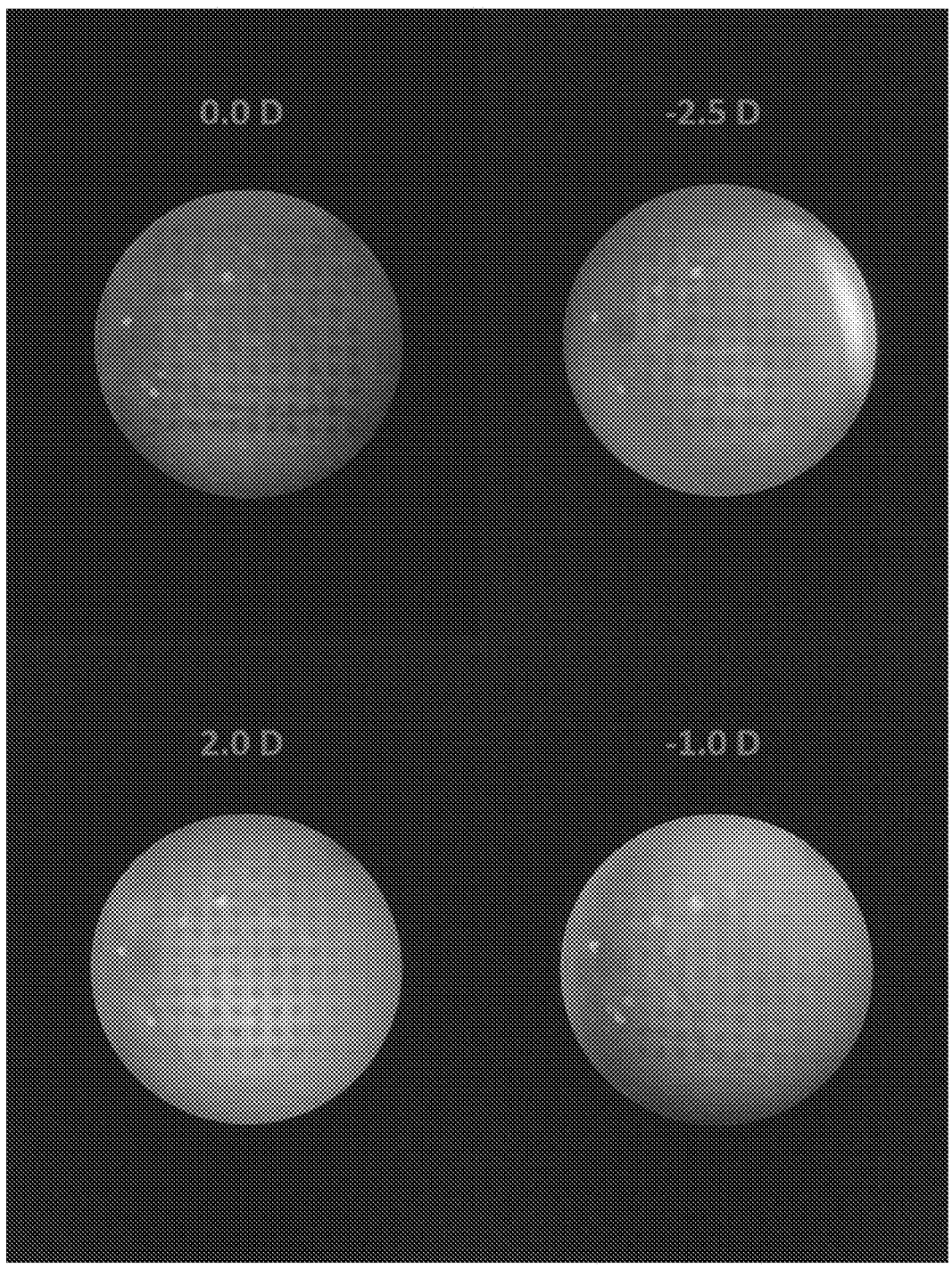
FIG. 11 shows, according to particular exemplary aspects of the present invention, four retinal images with the projected grid pattern from different cohort subjects. Self-reported refractive error is listed above each image.
Figure 12:
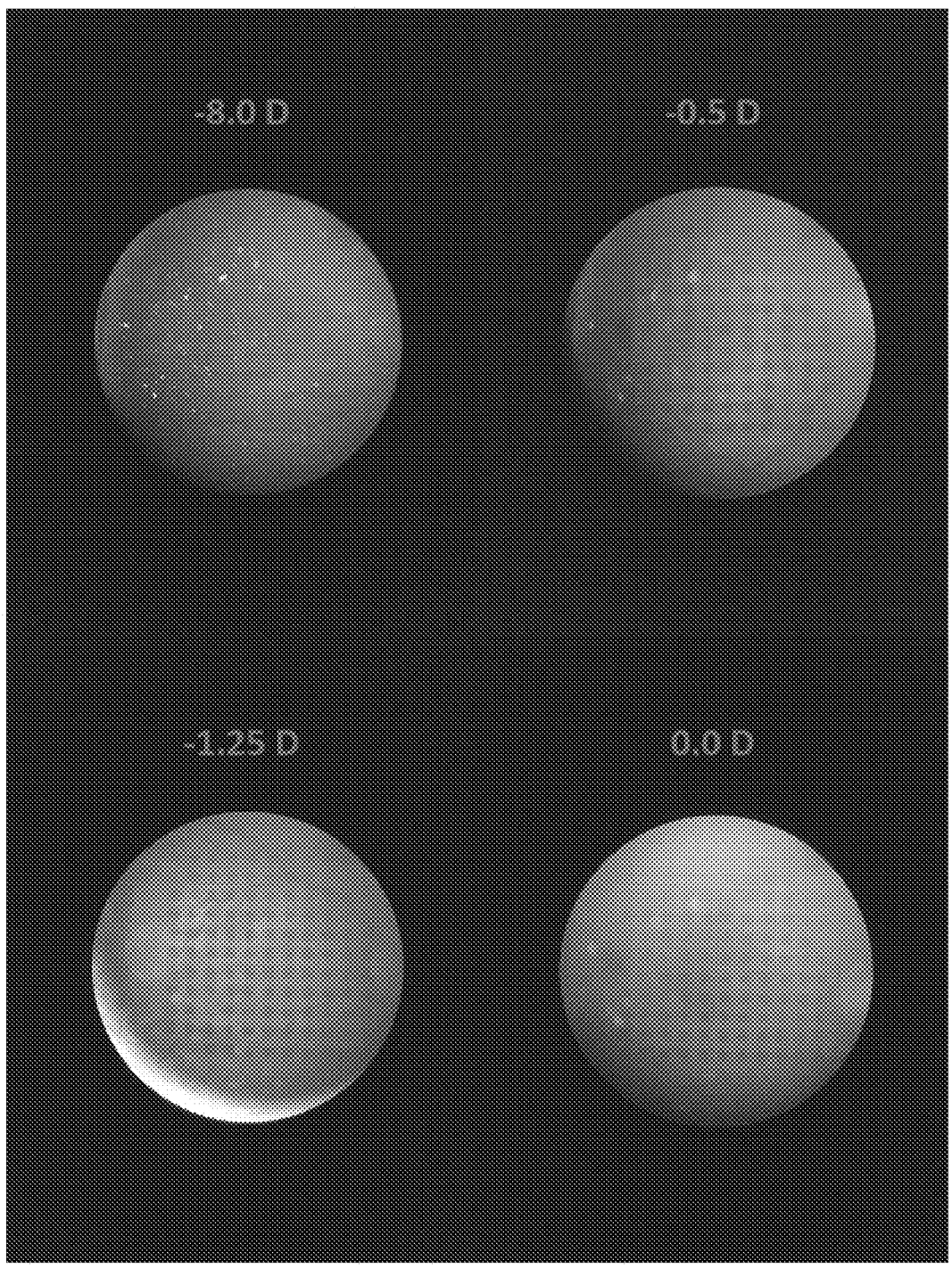
FIG. 12 shows, according to particular exemplary aspects of the present invention, four retinal images with the projected grid pattern from yet different cohort subjects. Self-reported refractive error is listed above each image.
Figure 13:
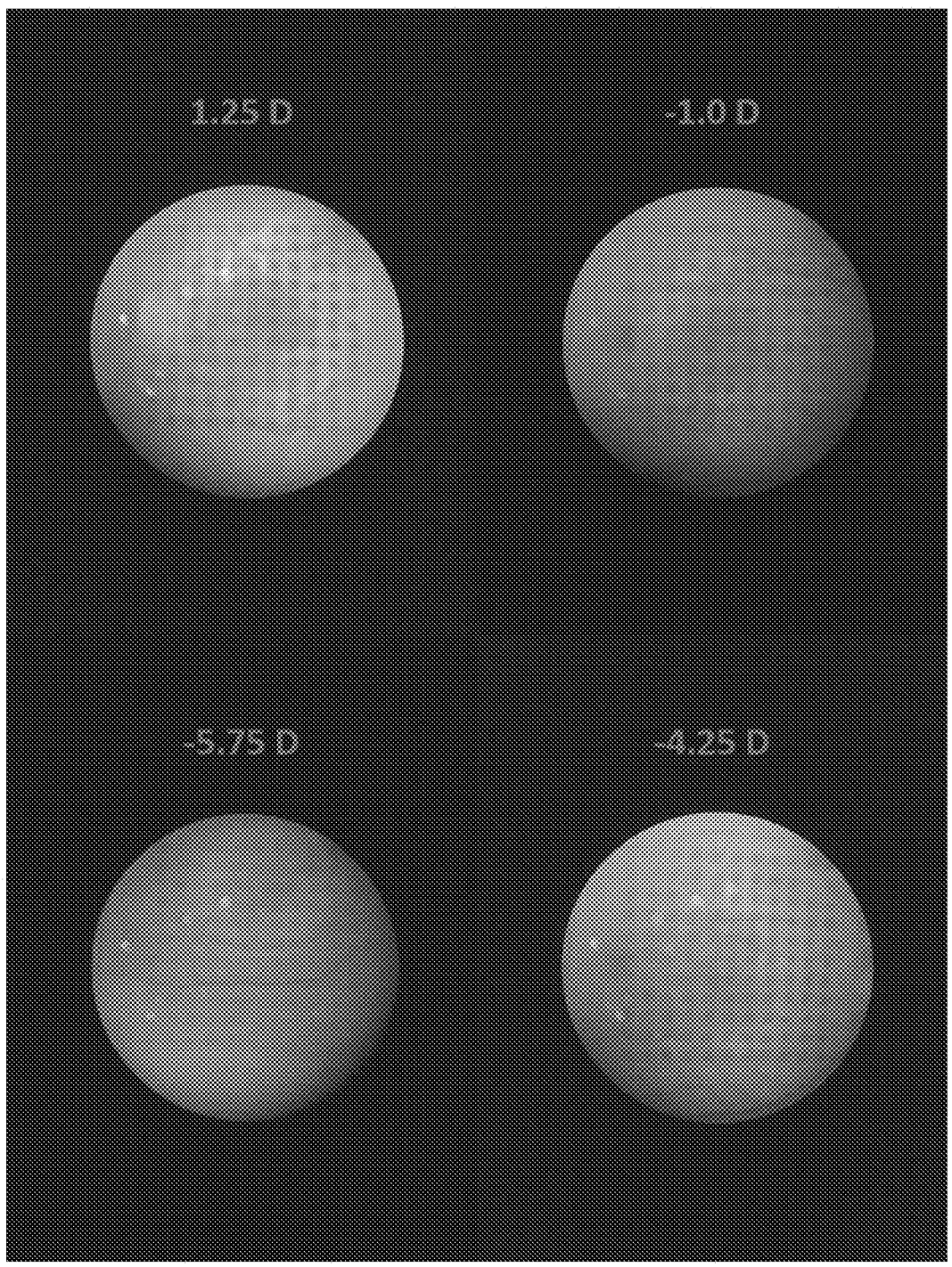
FIG. 13 shows, according to particular exemplary aspects of the present invention, four retinal images with the projected grid pattern from additional different cohort subjects. Self-reported refractive error is listed above each image.
Figure 14:
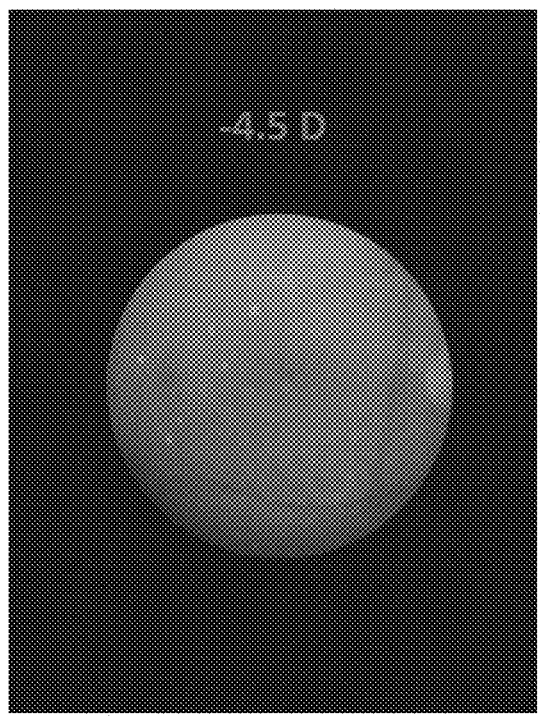
FIG. 14 shows, according to particular exemplary aspects of the present invention, the retinal image with the projected grid pattern of a final cohort subject. Self-reported refractive error is listed above the image.

FIGS. 10-14 demonstrate qualitative answers to two questions. Given that the location of the grid pattern is conjugate to the retina in the fundus camera system, it is indeed possible to resolve reasonably sharp target features for distortion measurement in human eyes. Second, by visual inspection, there appear to be differences between hyperopic, emmetropic, and myopic individuals in both ocular distortion patterns and overall image resolution of the grid pattern. FIG. 11 demonstrates this difference most clearly, where the +2 D subject appears to have more barrel distortion in the grid pattern than the more pincushion 0 D subject in the sub image above. The patterns of emmetropic and myopic subjects tend to show a more pincushion effect toward the periphery, but in some cases show a collapsing together of points in the central region. FIG. 12 demonstrates this effect of point collapse in the center for the −0.5 D subject and compared to the 0 D subject in the sub image below. Motivation for expanding the wavefront representation out to higher orders lies in reviewing the experimental data and seeing these combinations of distortion terms, creating complex distortion patterns.

Example 2

An Exemplary Target Consisted of a Known Pattern that Contains Useful Fiducials for Quantifying Ocular Distortion This exemplary working example illustrates use of a known grid pattern that contains useful fiducials for quantifying ocular distortion. Examples of such targets include, but are not limited to, a grid pattern, concentric circles, arrays of dots, etc.

FIGS. 10-14 show, according to particular exemplary aspects of the present invention, seventeen (17) retinal images with the projected grid pattern from cohort subjects. Self-reported refractive error is listed above each image.

Example 3

A Phase Target May be Placed in the Illumination Path of a Fundus Camera at a Location that is a Fourier Transform Plane of the Retina The systems and methods may comprise placing a phase target in the illumination path of a fundus camera at a location that is a Fourier transform plane of the retina, wherein the phase target may have a suitable pattern (e.g., grid pattern, concentric circles, arrays of dots, etc.) such that its Fourier transform creates a suitable amplitude pattern on the retina for measuring ocular distortion.

Example 4

Figure 15:
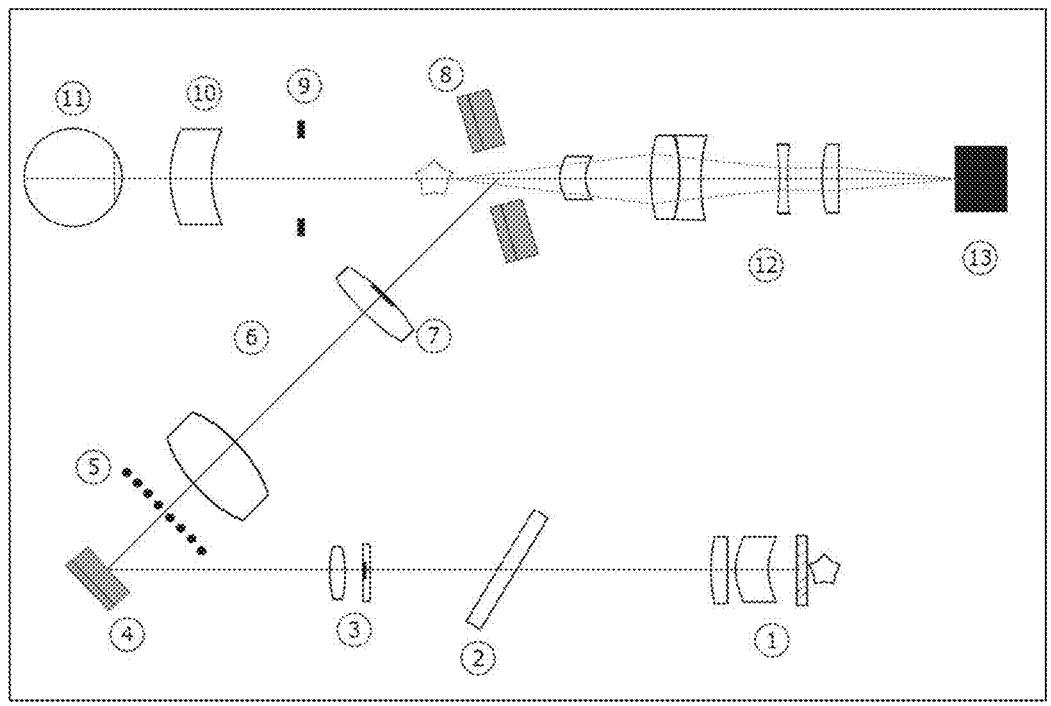
FIG. 15 shows, according to particular exemplary aspects of the present invention, the final imaging path for the modified fundus camera. An intermediate image of the retinal surface and grid target is located before holed mirror at location 8. The location of this intermediate image is different for subjects with any refractive error. A zoom lens system corrects for any added power induced by the eye under test.

An Image Sensor in the Imaging Path was Used to Record Images of the Target Projected onto the Retina FIG. 15, shows the final imaging path for the modified fundus camera. An intermediate image of the retinal surface and grid target is located before holed mirror at location 8. The location of this intermediate image is different for subjects with any refractive error. A zoom lens system corrects for any added power induced by the eye under test. FIG. 15 illustrates the final optical path that relays the intermediate image of the retinal surface to a detection plane at location 13. The imaging path, shown in orange, consists of a zoom lens configuration marked by location 12. Various degrees of ametropia will cause the intermediate image of the retina to form at different points along the optical axis in front of the holed mirror. The retinal image is passed through a series of lenses to correct the ametropia of the eye including two astigmatic lenses that combine to form a cylindrical lens of variable axis and power to correct for patient astigmatism (131). From the correction lenses the object pattern is sent to a doublet that begins a typical zoom lens system. Changing the spacing between the doublet, negative lens and positive lens, it is possible to compensate for the varied axial position of the intermediate retinal image. Thus, the focal length to the detection plane is altered to present a sharp image of the retina at the detection plane.

Example 5

Real-Time Image Processing Software that Examines Features in the Retinal Image Such as Blood Vessels was Used to Provide Autofocus of the Image and to Ensure Alignment of the Eye Between Consecutive Images; Blood Vessels were Kept in Focus and Tracked Over Subsequent Images To quantitatively show that there is variability between hyperopic, emmetropic, and myopic subjects, a testing criterion was created for the data processing of the grid pattern centroids.

First, each image selected for processing required the optic disc to appear on the right side of the image. Given that the right eye for each subject under test was used, this provides a roughly equivalent retinal area for investigation for each subject. In the case of the +2 D subject, whose left eye was imaged, the image was rotated about the vertical axis to place the optic disc on the right side of the image.

Second, three images of each subject are processed to create a mean for the fit distortion values.

Third, in each of the three images, the eye must not have rotated more than 3.5° between subsequent images.

The approximate field of view of the fundus camera is around 50° or 2020 pixels (e.g., on a cellphone sensor). By tracking a portion of a blood vessel in each of the selected images, the average pixel movement of the eye was recorded. Therefore, images where blood vessel jumps were less than 175 pixels and met the criterion of optic disc location, were selected as processing candidates for distortion fitting. A sample set of three images is shown in FIG. 16.

Figure 16:
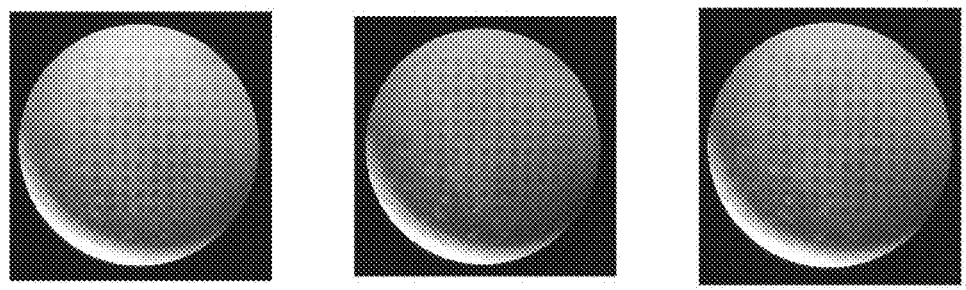
FIG. 16 shows, according to particular exemplary aspects of the present invention, three processing candidate images that meet the criterion for post-processing. It is of important note that the pattern does not deviate significantly even with small eye rotations, supporting that a stable, repeatable target can be imaged on the retina.

FIG. 16, shows, according to particular exemplary aspects of the present invention, three processing candidate images that meet the criterion for post-processing. It is of important note that the pattern does not deviate significantly even with small eye rotations, supporting that a stable, repeatable target can be imaged on the retina.

Example 6

Software Guided Alignment Assistance was Useful with Eye Tracking

One of the largest errors experienced in human imaging comes from camera and eye misalignment. Particular aspects of the present invention, provide for modifying a second-generation camera system with a more robust alignment package. For example, a minimally invasive eye tracking camera setup may be placed on the front of the system. Using near infrared (NIR) radiation, the pupil of the eye can be monitored, and the center of the pupil tracked using, e.g., the starburst method as one example of many eye tracking techniques. Capturing the eye in the NIR provides a high contrast pupil boundary for image processing while also minimizing ambient light noise during fundus imaging. Tracking pupil gaze direction allows for some eye orientation information and consequently, retinal area information.

Additional aspects, provide for monitoring the fundus camera body location relative to the head or chin rest position. For example, monitoring relative distance away from these fixed datums provides useful 3D spatial information of the camera pointing direction relative to gaze direction. Using a model eye on a laboratory bench, the system is calibrated with a known grid target pattern projected onto the retinal model eye. Translation stages and rotation stages placed at the center of rotation of the model eye are then used to displace the model eye in varying degrees while images of the target pattern are captured. After several runs, a database of ocular distortion images is captured and in human imaging, the database is accessed to correlate live images with eye model patterns. When the camera system identifies forms that are likely due to misalignment, image capture is functionality turned off to reduce the number of problematic or high error distortion patterns, flagged in the data set, or have a compensating mechanism which drives the system back into alignment.

Finally, auto detection suites may be implemented to capture and identify retinal features. By identifying retinal features such as blood vessels, the camera system can autofocus to ensure that image capture of the retinal surface is always well resolved. Tracking of these features may also ensure alignment by tracking the movement of features between subsequent images. If the eye rotates too far, or the head shifts during imaging, the software may flag images taken during these large movements or stop image capture functionality.

Example 7

Figure 17:
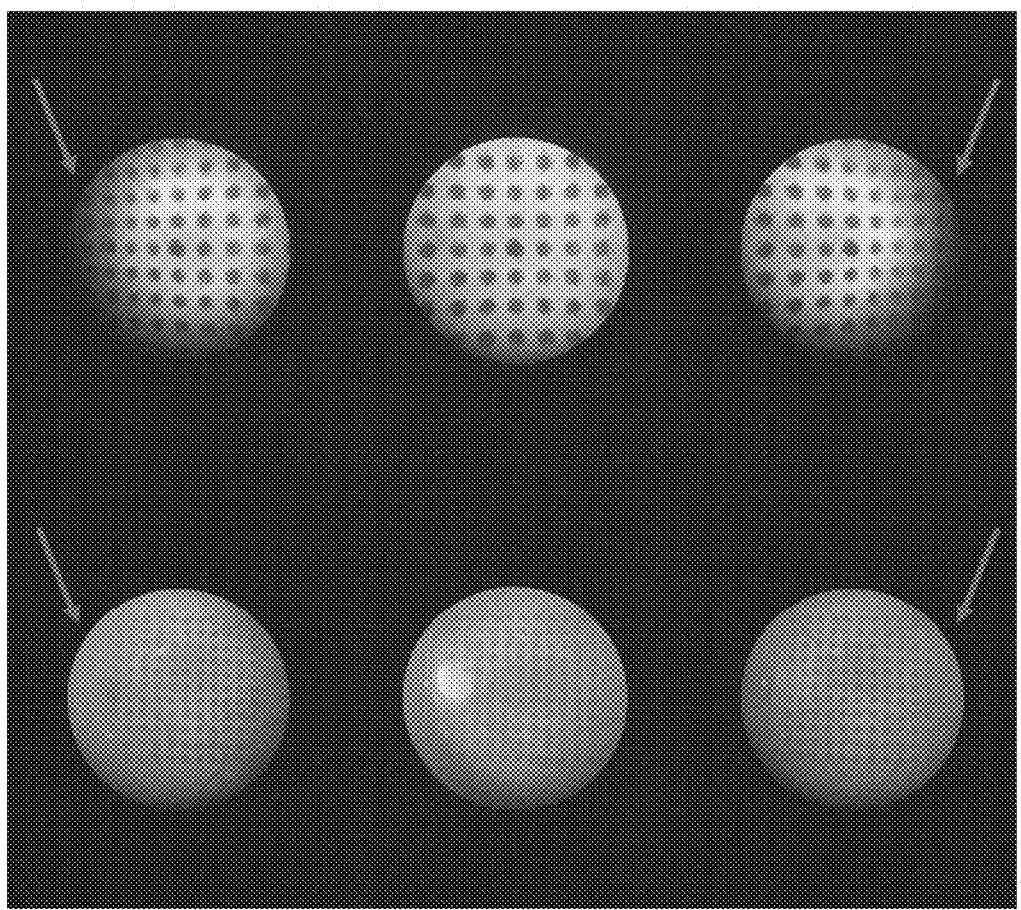
FIG. 17 shows, according to particular exemplary aspects of the present invention, that lateral misalignment with respect to the eye stop causes keystone distortion. Example images for the calibration system (top) and in a human subject (bottom). In the human subject, the corner opposite the vignetting side appears to pinch and blur.

Hardware and Software was Used to Track the Human Eye and Gaze Direction, Ensuring Eye Alignment, and Providing Useful Information on Eye Orientation During Measurement of Ocular Distortion FIG. 17, shows, according to particular exemplary aspects of the present invention, that lateral misalignment with respect to the eye stop causes keystone distortion. Example images for the calibration system (top) and in a human subject (bottom). In the human subject, the corner opposite the vignetting side appears to pinch and blur.

Recognizable patterns can indicate misalignment for correction, using the hardware and software described in Examples 5 and 6.

Example 8

Software was Used to Analyze the Captured Images and Automatically Identify Features in the Target Pattern, which Identified Features were then Compared to the Known Target Patter to Quantify the Amount of Ocular Distortion As discussed in Example 5, to quantitatively show that there is variability between hyperopic, emmetropic, and myopic subjects, a testing criterion was created for the data processing of the grid pattern centroids. First, each image selected for processing required the optic disc to appear on the right side of the image. Given that the right eye for each subject under test was used, this provides a roughly equivalent retinal area for investigation for each subject. In the case of the +2 D subject, whose left eye was imaged, the image was rotated about the vertical axis to place the optic disc on the right side of the image. Second, three images of each subject are processed to create a mean for the fit distortion values. Third, in each of the three images, the eye must not have rotated more than 3.5° between subsequent images.

The approximate field of view of the fundus camera is around 50° or 2020 pixels (e.g., on a cellphone sensor). By tracking a portion of a blood vessel in each of the selected images, the average pixel movement of the eye was recorded. Therefore, images where blood vessel jumps were less than 175 pixels and met the criterion of optic disc location, were selected as processing candidates for distortion fitting. A sample set of three images is shown in FIG. 16.

The data processing scheme to find the grid pattern centroids and fit to distortion wavefront errors follows a series of post processing steps that are completed using MATLAB numerical software. Processing dot centroids in, e.g., the human subject images is done in two steps, an automatic Fourier based method and a user defined clicking procedure.

A candidate image was loaded, cropped and resized to perform a computationally efficient Discrete Fourier Transform (DFT). Pixel coordinate space was transformed to real space with knowledge of, e.g., the cellphone sensor parameters. Similarly, the Fourier or frequency space domain was created from the real space coordinates and in consideration with Nyquist sampling theorem. A complex filtering function was incorporated in the raw image DFT to reduce intensity variation and suppress noise artifacts found on the retina.

Figure 18:
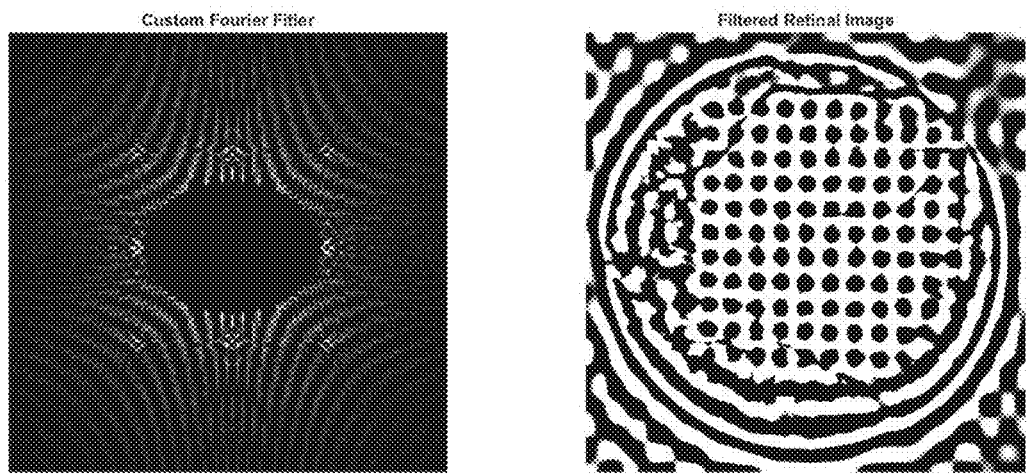
FIG. 18 shows, according to particular exemplary aspects of the present invention, a filtered Fourier Transform (FT) shown on the left with the binary resultant image of the retina shown on the right.

FIG. 18 shows, according to particular exemplary aspects of the present invention, a filtered Fourier Transform (FT) shown on the left with the binary resultant image of the retina shown on the right.

The Fourier domain shows the frequency separation of the grid pattern related to the dot pitch, which is the critical information necessary to calculate centroid center locations. Uneven illumination, color, and noise artifacts such as blood vessels can be suppressed relatively well through this method. In this exemplary instance optimization of the complex filter function was not performed as each subject case had varied levels of dot image quality. Furthermore, no image enhancement related to dot shape or size was performed due to the variability in resolution capability for each subject. Once the binary image was formed, an internal MATLAB algorithm was used to identify centroid locations.

Figure 19:
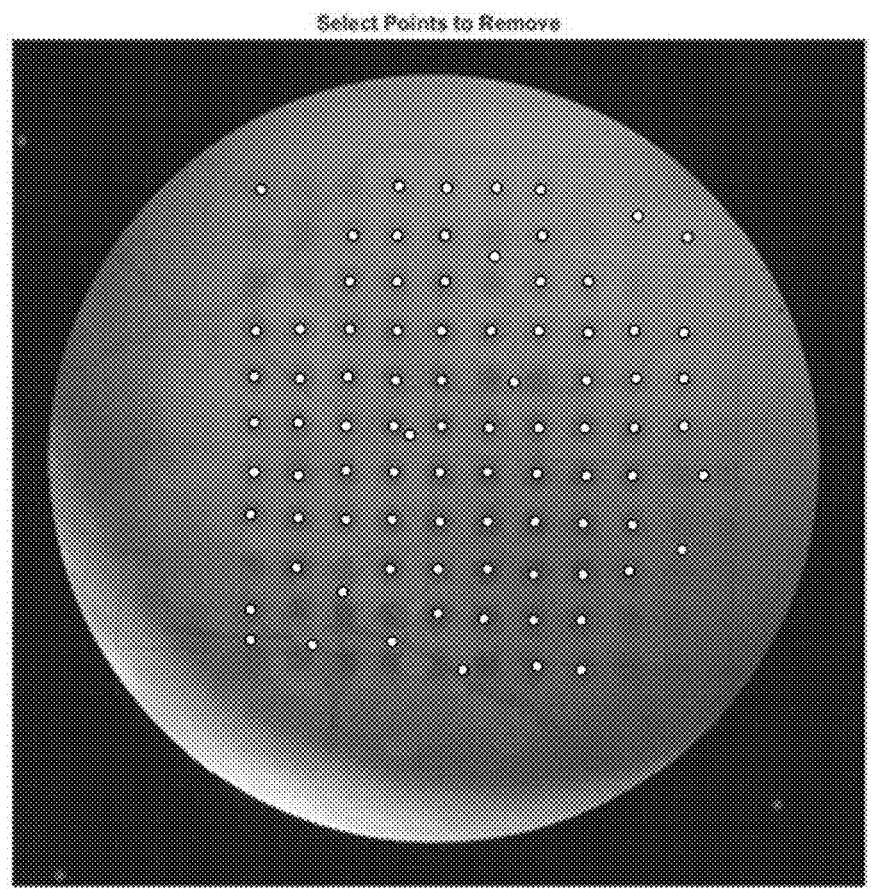
FIG. 19 shows, according to particular exemplary aspects of the present invention, centroid centers marked in white that were found by the internal centroid algorithm. Incorrect or misinterpreted centroid values are also present in the image and indicate false positive centers.

Contiguous matrices used a nearest neighbor approach to identify connected components in the binary image. Careful selection of component size yields locations of dot centers as shown in FIG. 19. Approximately, 25%-50% of image points can be captured automatically sign this automated method.

FIG. 19 shows, according to particular exemplary aspects of the present invention, centroid centers marked in red that were found by the internal centroid algorithm. Incorrect or misinterpreted centroid values are also present in the image and indicate false positive centers. The false positives for centroids seen in FIG. 19 provide the motivation for the second centroid center locating procedure, user hand clicked points. While automatic detection relies on mathematical weighting do determine centroids, the reality of false positives requires the aid of the human eye. While also correcting for these erroneous centroid locations, it is possible to expand the data set by user clicking the remaining centers for increased point sampling in the image. Once the final center coordinate location has been recorded, points are passed through a sorting algorithm to orient point (1,1) in the matrix as the upper left most point all the way through point (11,11). This ensures that proper field coordinates can be identified.

Typically, distortion values are reported such that the distorted image or target is referenced to a nominal or undistorted object. To create a nominal or undistorted reference grid, where the center location of centroids should have been located, a center spacing value was calculated for each image processed. The spacing between the center dot of the grid pattern at position (6,6) and the four nearest neighbors were averaged to create the nominal grid spacing, centered at the (6,6) position and illustrated in FIG. 20. The assumption made for the reference grid is that the distortion around the (6,6) point should be low given that this is close to the optical axis of the fundus camera system.

Figures 20, 21:
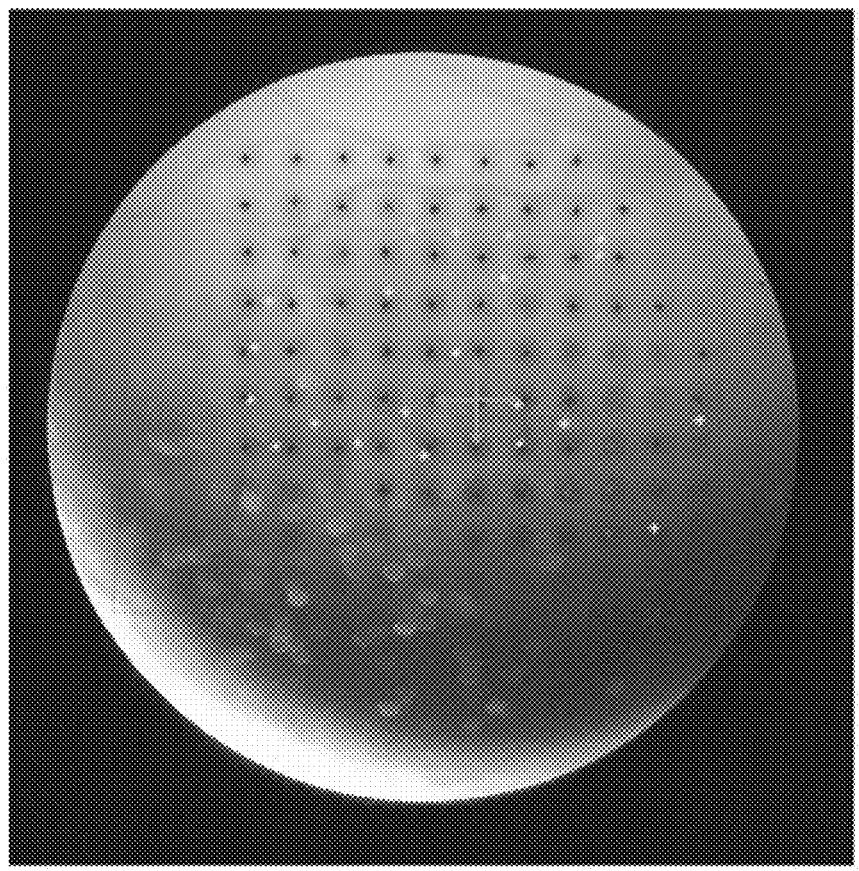
FIG. 20 shows, according to particular exemplary aspects of the present invention, that the method for determining the undistorted reference grid is done by taking the center dot of the grid pattern at (6,6) and average the four nearest neighbor distances seen as black dots. Removed false-positive points (white) can be viewed with the automatically found centers (light gray) and the user hand-clicked centers (dark gray).
FIG. 21 shows, according to particular exemplary aspects of the present invention, Table 1; repeatability results for automatic and manual center dot processing. All number are in units of pixel space coordinates. Commentary on fit errors related to spacing values is presented later.

FIG. 20 shows, according to particular exemplary aspects of the present invention, that the method for determining the undistorted reference grid is done by taking the center dot of the grid pattern at (6,6) and average the four nearest neighbor distances seen in dark gray. Removed false-positive points (white) can be viewed with the automatically found centers (light) and the user hand-clicked centers (dark gray).

The center hand clicking method can raise concerns of error in center location values. User bias, accuracy, fatigue and image noise all contribute to potential error. To understand the type of error that could be induced during the hand clicked processing a repeatability test was devised. Using a nominal image like the one shown in FIG. 20, the automated and manual processing was completed back to back six times. In each of the six runs, the number of automatically found points was increased or decreased to see if there was influence on having a majority of the found centers come from hand clicking.

FIG. 21 (Table 1) shows/reports repeatability results for automatic and manual center dot processing, and lists the number of automatically found points and the center spacing of the resulting distorted center locations. All number are in units of pixel space coordinates. It was determined that the two-stage process of center location was sufficient for processing the entirety of the human retina dataset.

Coefficient Fitting and Results. With the assumption that the human eye is a rotationally non-symmetric optical system and using the wavefront expansion from Barakat, the processed centers from each subject was fit to $4^{th}$ order distortion coefficients in x and y. Though this text extends the wavefront error out to the $6^{th}$ order, it was found that the least squares fitting was over constrained causing numerical error in lower fit orders.

Using the nominal spacing value to determine nominal grid coordinates $(x_o, y_o)$ a polynomial matrix A, is formed to evaluate the distorted center coordinates (x,y). The nominal grid points $(x_o, y_o)$ and the distorted grid points (x,y) share a common center point which is $(x_6, y_6)$. Subtracting the center point from both sets of coordinates creates a Cartesian pixel space of positive and negative coordinates. The following least-squares minimization equation to find the distortion coefficients for (x,y) is shown in Equation 4.1 below.

$$A_x \backslash b_x = \begin{bmatrix} x_{o,1} & y_{o,1} & x_{o,1}^2 & \cdots & x_{o,1}^3 \\ \vdots & \vdots & \vdots & \ddots & \vdots \\ x_{o,n} & y_{o,n} & x_{o,n}^2 & \cdots & x_{o,n}^3 \end{bmatrix} \begin{bmatrix} x_1 \\ \vdots \\ x_n \end{bmatrix} = \begin{bmatrix} F_{x,1} \\ \vdots \\ F_{x,9} \end{bmatrix} \quad 4.1$$

$$A_y \backslash b_y = \begin{bmatrix} x_{o,n} & y_{o,1} & x_{o,1}^2 & \cdots & x_{o,n}^3 \\ \vdots & \vdots & \vdots & \ddots & \vdots \\ x_{o,n} & y_{o,n} & x_{o,n}^2 & \cdots & x_{o,n}^3 \end{bmatrix} \begin{bmatrix} y_1 \\ \vdots \\ y_n \end{bmatrix} = \begin{bmatrix} F_{y,1} \\ \vdots \\ F_{y,9} \end{bmatrix}$$

In Equation 4.1, n is equal to the number of dot centers found, with a maximum of 121 found centers for the 11×11 target grid but the number of points varies between subjects. $F_{x,y}$ represent the x and y distortion terms for the $4^{th}$ order wavefront error expansion. These $F_{x,y}$ coefficients represent the Barakat B-D labeling coefficients and will be reported as such. Thus, 18 independent coefficients are fit in this process.

The $10^{th}$ subject of this study was chosen at random do demonstrate the variance in coefficient values across the three processed images. The coefficient values for each processed image for all 18 coefficients are shown in FIGS. 22-24.

Figure 22:
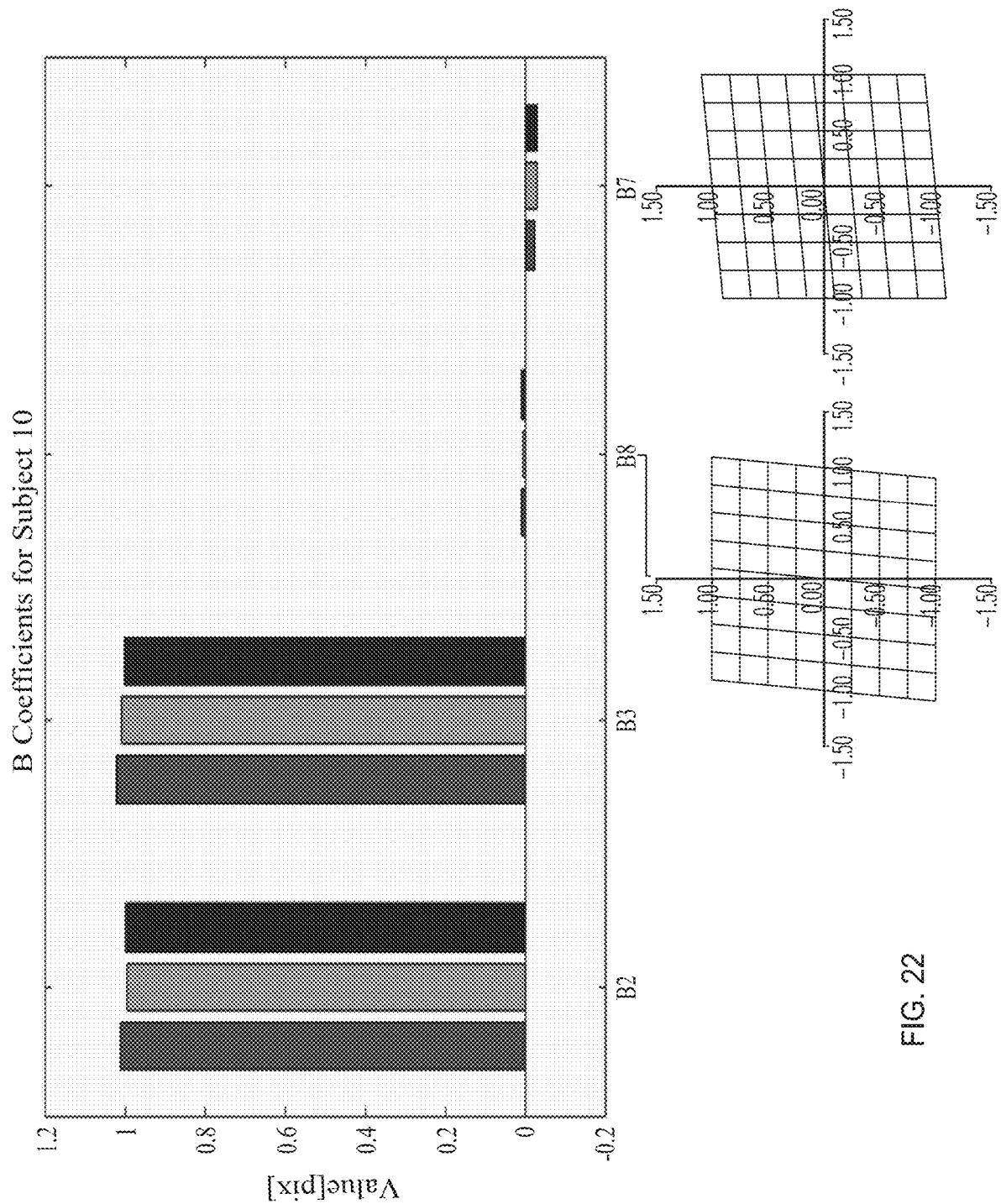
FIG. 22 shows, according to particular exemplary aspects of the present invention, linear B coefficient values for human subject 10. Note $B_2$ and $B_3$ correspond to x and y linear magnification respectively. Fit values are stable and of reasonable magnitude for each processed image.

FIG. 22 shows, according to particular exemplary aspects of the present invention, linear B coefficient values for human subject 10. Note $B_2$ and $B_3$ correspond to x and y linear magnification respectively. Fit values are stable and of reasonable magnitude for each processed image.

Figure 23:
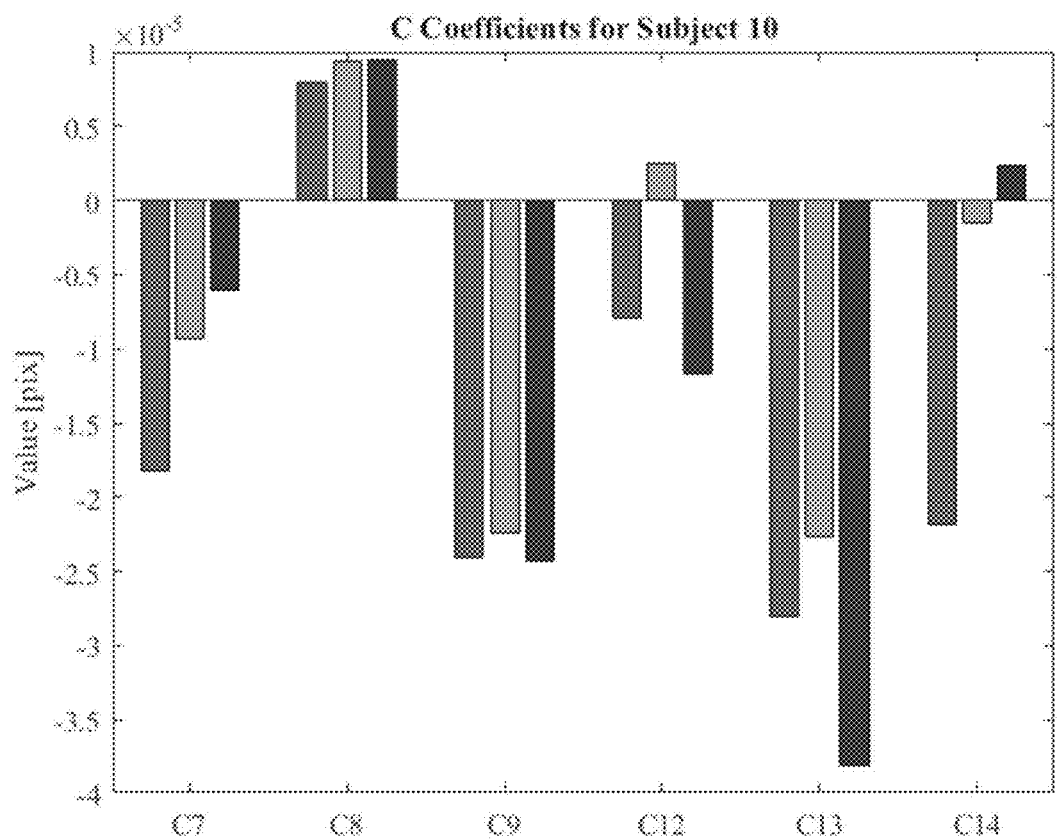
FIG. 23 shows, according to particular exemplary aspects of the present invention, quadratic C coefficient values for subject 10. Fit values for ($C_7$, $C_8$, $C_9$, $C_{13}$) are stable and of reasonable magnitude for each processed image. Fit values for ($C_{12}$, $C_{14}$) are unstable in sign and magnitude making them inconclusive representations of image distortion.
Figure 23:
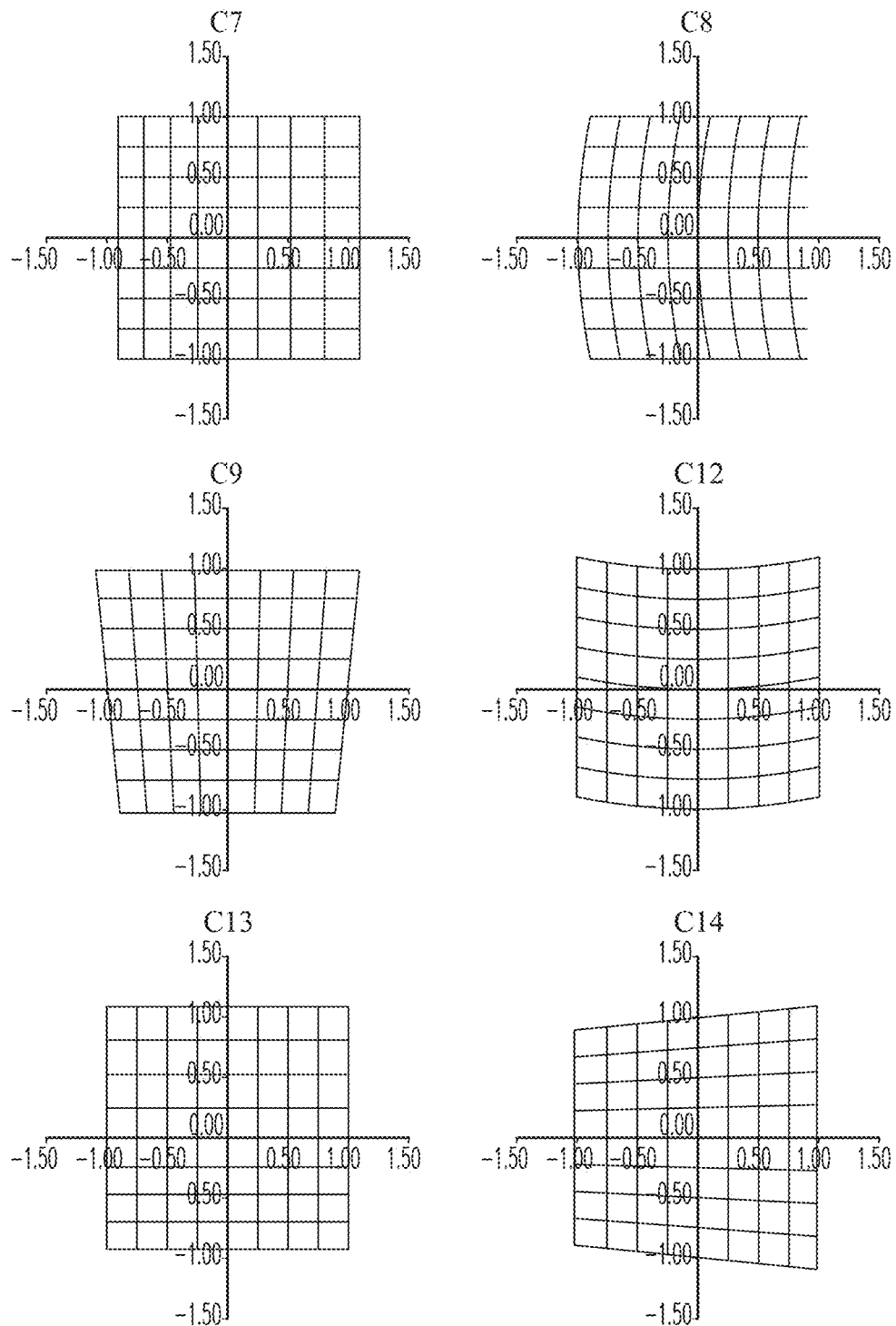

FIG. 23 shows, according to particular exemplary aspects of the present invention, quadratic C coefficient values for subject 10. Fit values for $(C_7, C_8, C_9, C_{13})$ are stable and of reasonable magnitude for each processed image. Fit values for $(C_{12}, C_{14})$ are unstable in sign and magnitude making them inconclusive representations of image distortion.

Figure 24:
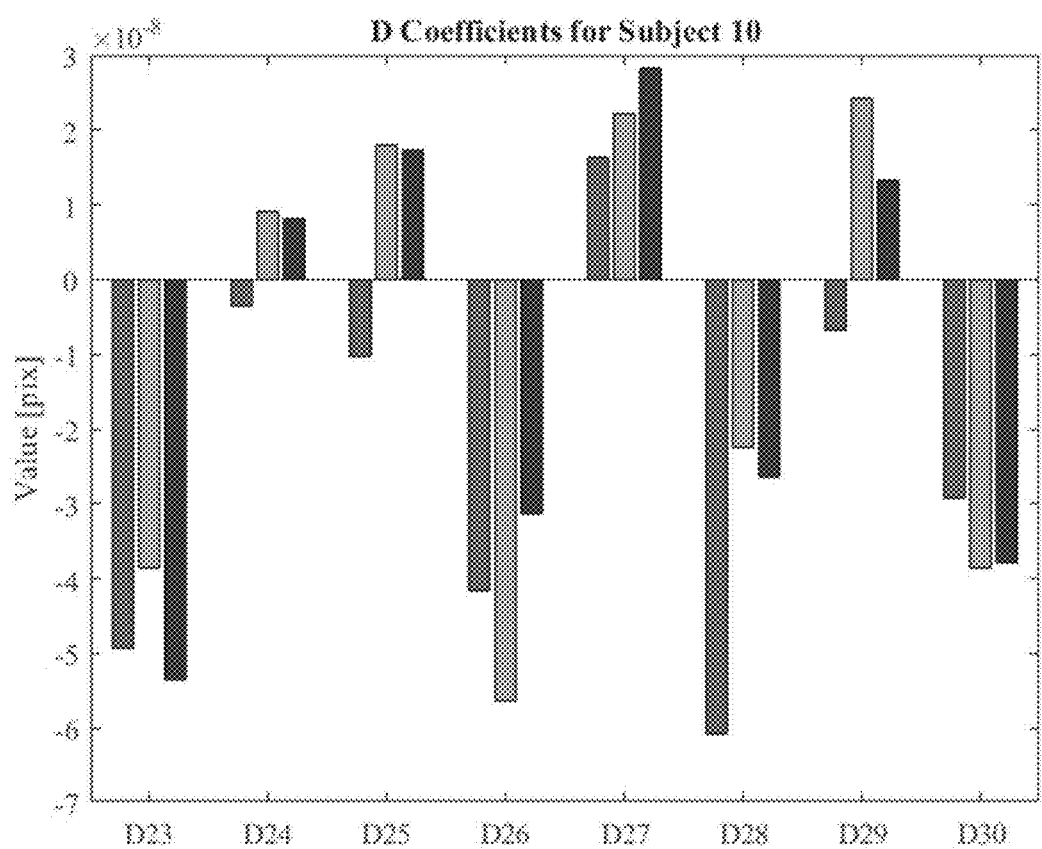
FIG. 24 shows, according to particular exemplary aspects of the present invention, Cubic D coefficient values for subject 10. Fit values for ($D_{23}$, $D_{26}$, $D_{27}$, $D_{28}$, $D_{30}$) are stable and of reasonable magnitude for each processed image. Fit values for ($D_{24}$, $D_{25}$, $D_{29}$) are unstable in sign and magnitude making them inconclusive representations of image distortion.
Figure 24:
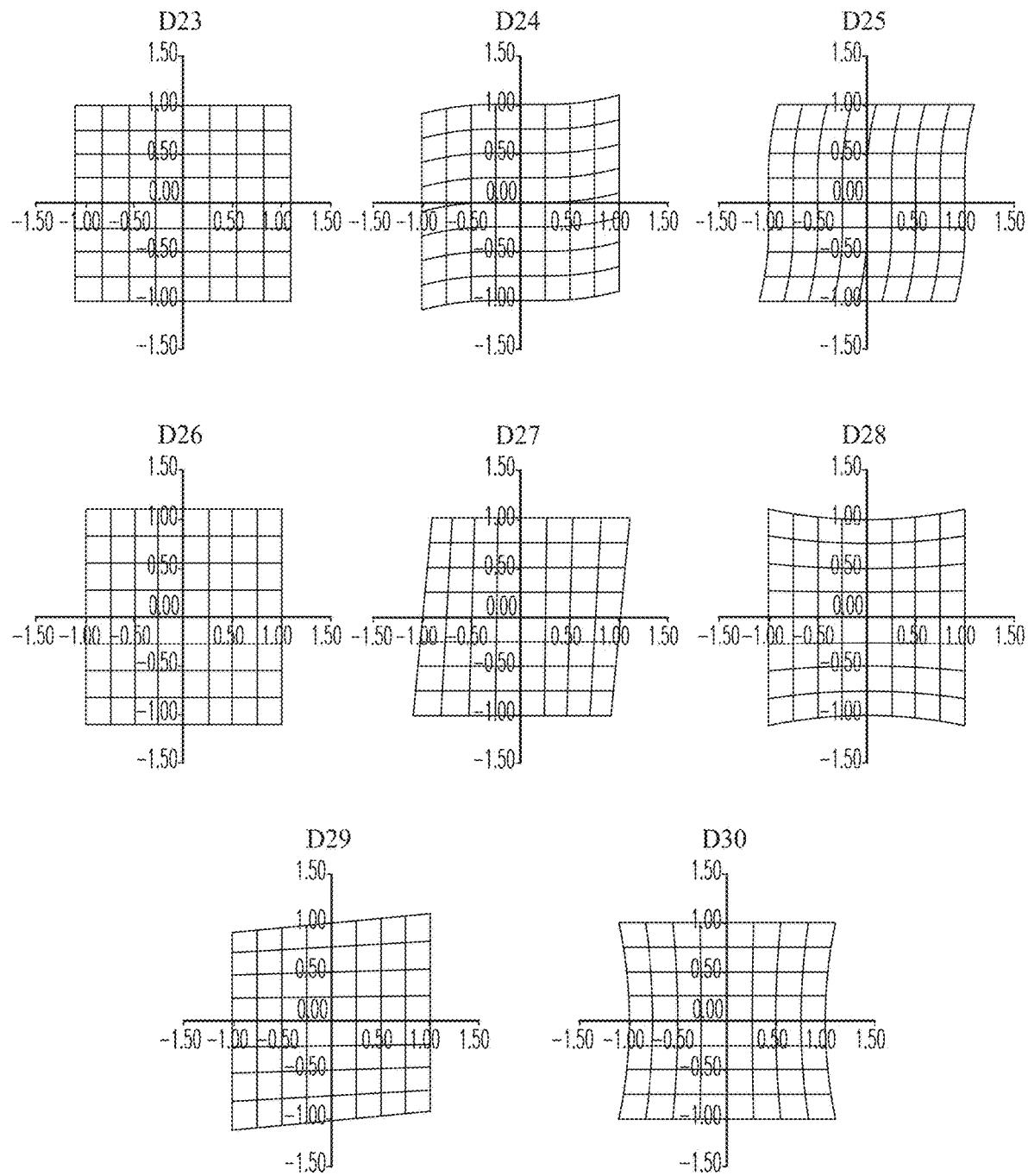

FIG. 24 shows, according to particular exemplary aspects of the present invention, Cubic D coefficient values for subject 10. Fit values for $(D_{23}, D_{26}, D_{27}, D_{28}, D_{30})$ are stable and of reasonable magnitude for each processed image. Fit values for $(D_{24}, D_{25}, D_{29})$ are unstable in sign and magnitude making them inconclusive representations of image distortion.

While over the three processed images of FIGS. 22-24, some coefficients flip sign or span zero, and the trustworthiness of these coefficients at representing their corresponding distortion of the subjects is therefore inconclusive, most coefficients nonetheless appear to be stable across the three images, bringing confidence to the fitting as well as supporting that representing complex distortion of the eye as components is be a valid approach in understanding ocular distortion.

From the three images processed for each subject, the mean and standard deviation of each coefficient was found. Mean values for each subject are plotted against their self-reported refractive error. Given the system sensitivity and low number of processed images, only four distortion terms ($D_{23}$, $D_{26}$, $D_{28}$, $D_{30}$) related to building $3^{rd}$ order radial distortion are discussed for the entire subject population. It should be noted that beyond the four terms, a few other distortion term values exhibited potential trends with respect to refractive error.

For the $D_{26}$ and $D_{28}$ coefficients, no significant trend occurred in the mean data set across the population. The $D_{23}$ coefficients exhibited and interesting nature of two pooled value groups, one around $-3e^{-07}$ and another around $-6.5e^{-07}$. This distortion coefficient can be thought of as an increase in point spacing in the nasal-temporal meridian, where separation is largest at the maximum field extent. Lastly, $D_{30}$ coefficients exhibited a grouping around a value of $-5e^{-08}$, which would suggest a population centered around some common level of barrel distortion in the nasal-temporal meridian.

The next logical step combines the four distortion terms above into a relative value of radial distortion. In most literature and in practice, radial distortion is calculated as a percentage in the form of a distance ratio of the residual movement. The distance from a center location to the nominal location of the maximum field point is compared to the distance from center of the distorted maximum field coordinate. Equation 4.2 below describes the formula used to calculate the percent distortion, where $r=\sqrt{x^2-y^2}$.

$$\%D = \frac{r_{distorted} - r_{nominal}}{r_{nominal}} * 100 \qquad 4.2$$

The nominal spacing for each run was used to build the nominal grid points. The mean of ($D_{23}$, $D_{26}$, $D_{28}$, $D_{30}$) was, applied to the $4^{th}$ order wavefront error equation with ($B_2=B_3=1$) and the nominal grid point as seed ($x_o, y_o$) coordinates. The maximum field coordinate along the diagonal of the square grid of points was used to calculate the radial distortion percentage. A plot of the mean percent distortion for the entire refractive population is shown in FIGS. 25A and 25B, along with the percent distortion found from the simulated population.

Figure 25A:
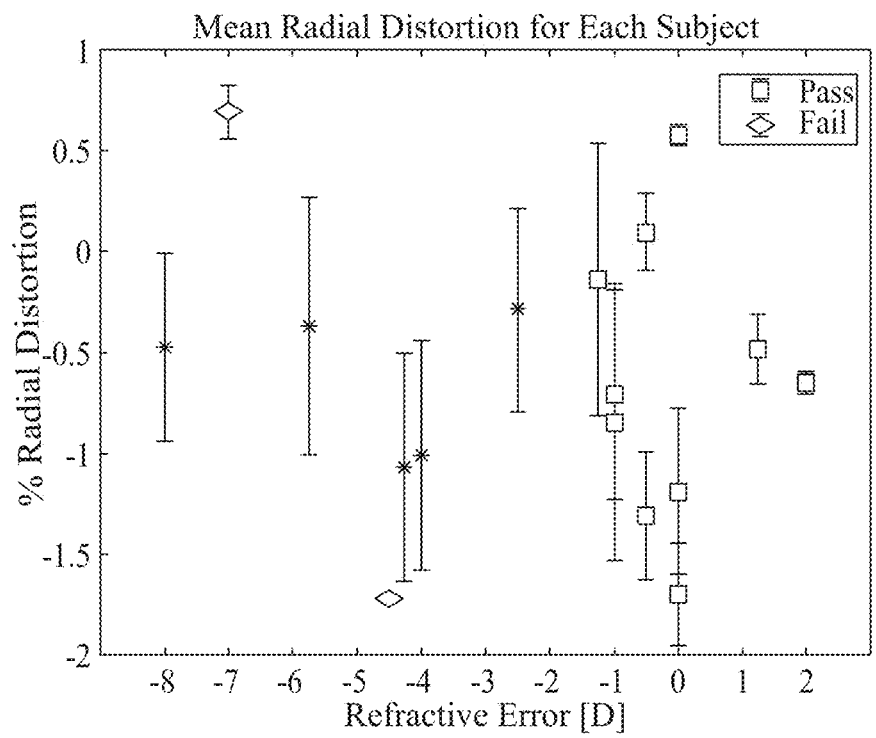
FIGS. 25A and 25B show, according to particular exemplary aspects of the present invention, mean radial distortion as a percentage plotted against the subject refractive error (FIG. 25A) and the simulated population radial distortion plotted against the subject refractive error (FIG. 25B). The square □ and diamond ◇ markings indicate strongly resolved and weak or blurred dot patterns respectively. The * markers in black correspond to subjects who had one or more radial distortion coefficient values span zero, indicating inconclusive results.
Figure 25B:
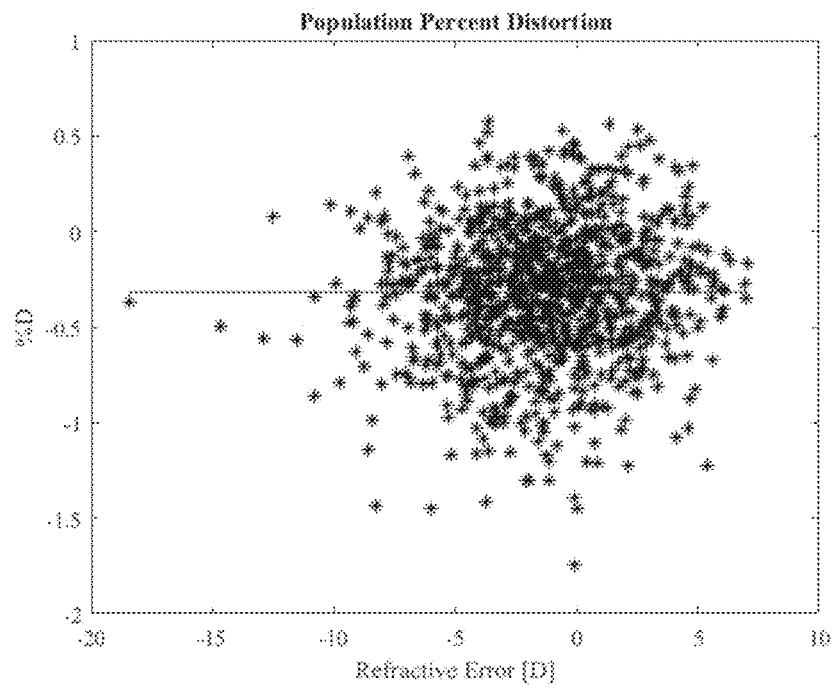

FIGS. 25A and B show, according to particular exemplary aspects of the present invention, mean radial distortion as a percentage plotted against the subject refractive error (FIG. 25A) and the simulated population radial distortion plotted against the subject refractive error (FIG. 25B). The square □ and diamond ◇ markings indicate strongly resolved and weak or blurred dot patterns respectively. The markers in black correspond to subjects who had one or more radial distortion coefficient values span zero, indicating inconclusive results.

The amount of radial distortion for the population appears to be around −0.5% barrel distortion after the 0.5% pincushion camera distortion offset is applied from calibration. Subjects who had one or more of their radial distortion terms be both positive and negative over the three processed images, were found in subjects of higher levels of myopia, perhaps reflecting limitations of an off the shelf camera configuration in measuring ocular distortion for individuals of higher myopia. Nonetheless, the data set from the human trials appears to match that of the simulated population.

Two new postulates can be raised from inspection of the radial distortion in FIGS. 25A and 25B. First, it may be that the eye grows, reshaping ocular components, to reach zero radial distortion or some minute value of barrel distortion in older age. Given that humans see a 3D world in only 2D, perhaps a similar compensation to null distortion is occurring in the brain for flat plane imaging as this fundus camera system does, where distortion values slightly out of some threshold set into motion mechanisms for eye growth. Second, the role of retinal curvature may play an important role in local distortion and visual perception. The variability of retinal curvatures coupled with the variability in ocular components could be an indicator for the data spread seen in the emmetropic and hyperopic subjects. Perhaps, the size, shape, and spacing of ocular components for each individual needs to reach minimum level for that given individual. It may be the case that some individuals can tolerate higher or lower levels of ocular distortion without causing eye growth leading to refractive development.

To evaluate the effectiveness of least squares fitting of distortion points to the $4^{th}$ order wavefront error function, a series of figures as well as RMS distance error was calculated for the fit points of all subjects. The $2^{nd}$ order fit, rebuilds the distorted wavefront points using only the linear B coefficients and nominal grid point locations. The $3^{rd}$ order fit and $4^{th}$ order fit are found using the same procedure but with the quadratic C coefficients and cubic D coefficients respectively.

The convergence was quite strong at the $4^{th}$ order wavefront error, leaving only higher frequency shifts present at certain field locations. This high order distortion is likely caused by local retinal curvature deviations. Though the representative coefficients for the $5^{th}$ and $6^{th}$ order wavefront error were calculated, it was discovered that the fitting was not numerically stable at these orders. Increasing the number of sampling points on the grid would potentially allow of numerical stability in the least squares fitting to higher orders, capturing the high frequency distortion. Transitioning to a normalized coordinate space may also improve numerical stability.

A numerical measure of fit was performed for all subjects related to the distance separation in pixels of fit points and distorted points. The residual distance between these two coordinates is reported as mean RMS error described by Equation 4.3 and shown graphically in FIG. 26. All subjects monotonically decrease as fit order increases with some subjects fitting much stronger than others. The deviation between subjects is related to the uncertainty in determining dot location due to blurred or weak dots, low resolved distortion point count, or presence of high order distortion beyond the $4^{th}$ order.

$$RMS\ \text{Fit Error} = \sqrt{\frac{\sum \sqrt{(x_{fit}-x_{distort})^2 + (y_{fit}-y_{distort})^2}}{\#\ \text{of points found}}} \qquad 4.3$$

Figure 26:
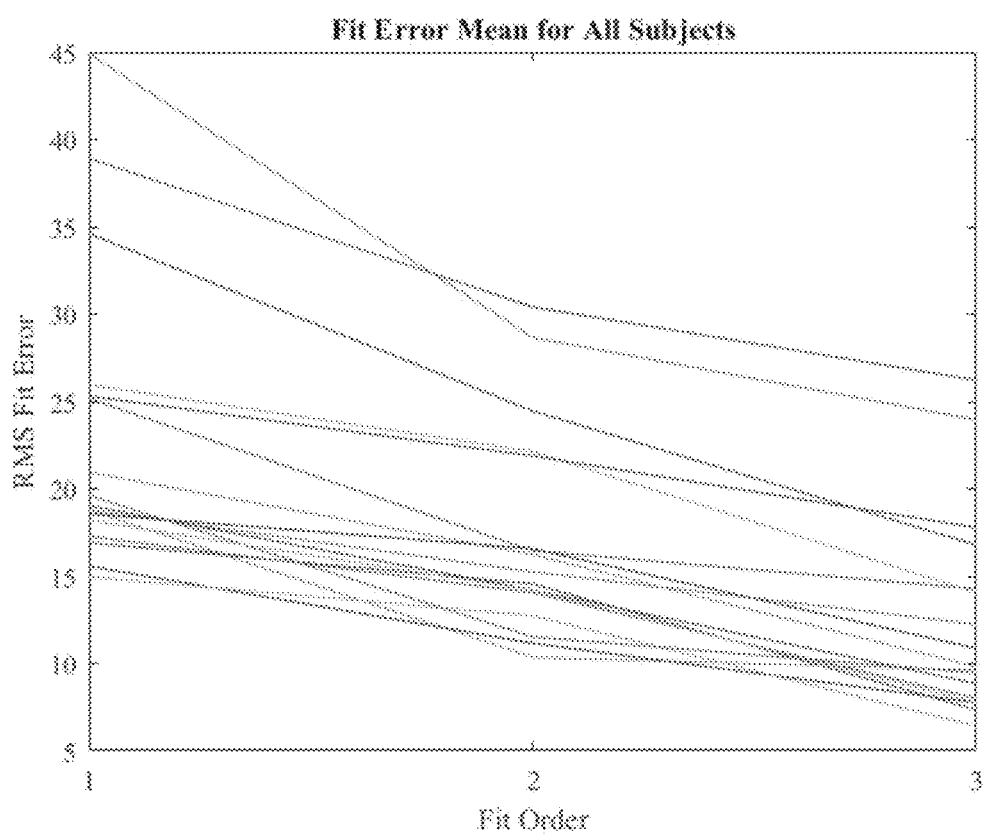
FIG. 26 shows, according to particular exemplary aspects of the present invention, mean RMS Fit error for all subjects. All subjects see improved fitting out the $4^{th}$ order wavefront error. Error units are in pixels. Larger error is attributed to weak dot contrast, low numbers of points found, and higher order distortion.

FIG. 26 shows, according to particular exemplary aspects of the present invention, mean RMS Fit error for all subjects. All subjects see improved fitting out the $4^{th}$ order wavefront error. Error units are in pixels. Larger error is attributed to weak dot contrast, low numbers of points found, and higher order distortion.

Computing Device

Figure 28:
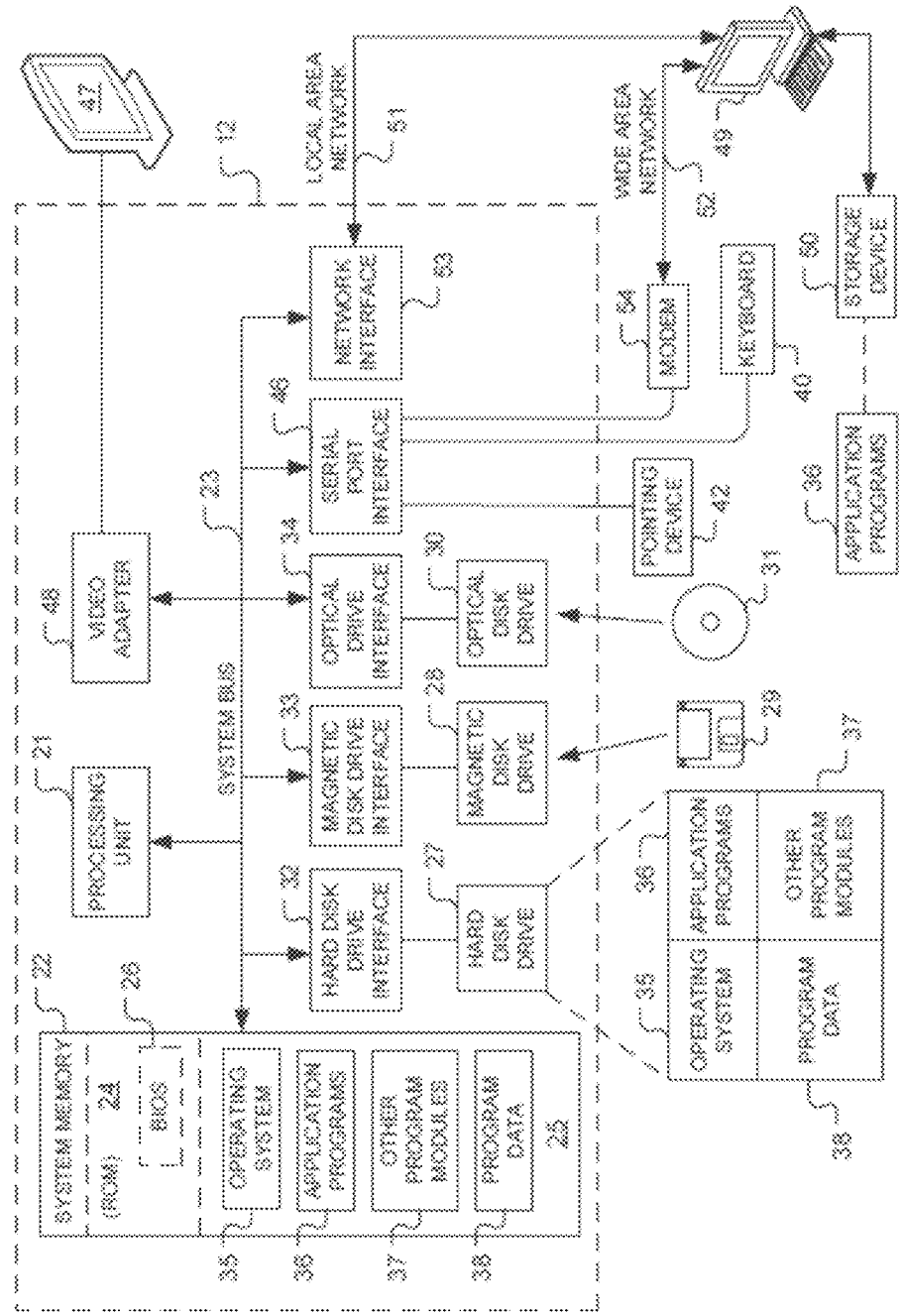
FIG. 28 shows an exemplary block diagram of hardware and an operating environment in conjunction with which implementations of the disclosed methods for measuring ocular distortion may be practiced.

FIG. 28 is a block diagram of hardware and an operating environment in conjunction with which implementations of the disclosed methods for measuring ocular distortion may be practiced. The description of FIG. 28 is intended to provide a brief, general description of suitable computer hardware and a suitable computing environment in which implementations may be practiced. Although not required, implementations are described in the general context of computer-executable instructions, such as program modules, being executed by a computer, such as a personal computer. Generally, program modules include routines, programs, objects, components, data structures, etc., that perform particular tasks or implement particular abstract data types.

Moreover, those of ordinary skill in the art will appreciate that implementations may be practiced with other computer system configurations, including the mobile communication device 300 (see FIG. 8), hand-held devices, multiprocessor systems, microprocessor-based or programmable consumer electronics, network PCs, minicomputers, mainframe computers, and the like. Implementations may also be practiced in distributed computing environments (e.g., cloud computing platforms) where tasks are performed by remote processing devices that are linked through a communications network. In a distributed computing environment, program modules may be located in both local and remote memory storage devices.

The exemplary hardware and operating environment of FIG. 28 includes a general-purpose computing device in the form of the computing device 12. By way of non-limiting examples, the computing device 12 may be implemented as a laptop computer, a tablet computer, a web enabled television, a personal digital assistant, a game console, a smartphone, a mobile computing device, a cellular telephone, a desktop personal computer, a blade computer, and the like.

The computing device 12 includes a system memory 22, the processing unit 21, and a system bus 23 that operatively couples various system components, including the system memory 22, to the processing unit 21. There may be only one or there may be more than one processing unit 21, such that the processor of computing device 12 includes a single central-processing unit ("CPU"), or a plurality of processing units, commonly referred to as a parallel processing environment. When multiple processing units are used, the processing units may be heterogeneous. Byway of a non-limiting example, such a heterogeneous processing environment may include a conventional CPU, a conventional graphics processing unit ("GPU"), a floating-point unit ("FPU"), combinations thereof, and the like.

The computing device 12 may be a conventional computer, a distributed computer, or any other type of computer.

The system bus 23 may be any of several types of bus structures including a memory bus or memory controller, a peripheral bus, and a local bus using any of a variety of bus architectures. The system memory 22 may also be referred to as simply the memory, and includes read only memory (ROM) 24 and random access memory (RAM) 25. A basic input/output system (BIOS) 26, containing the basic routines that help to transfer information between elements within the computing device 12, such as during start-up, is stored in ROM 24. The computing device 12 further includes a hard disk drive 27 for reading from and writing to a hard disk, not shown, a magnetic disk drive 28 for reading from or writing to a removable magnetic disk 29, and an optical disk drive 30 for reading from or writing to a removable optical disk 31 such as a CD ROM, DVD, or other optical media.

The hard disk drive 27, magnetic disk drive 28, and optical disk drive 30 are connected to the system bus 23 by a hard disk drive interface 32, a magnetic disk drive interface 33, and an optical disk drive interface 34, respectively.

The drives and their associated computer-readable media provide nonvolatile storage of computer-readable instructions, data structures, program modules, and other data for the computing device 12. It should be appreciated by those of ordinary skill in the art that any type of computer-readable media which can store data that is accessible by a computer, such as magnetic cassettes, flash memory cards, solid state memory devices ("SSD"), USB drives, digital video disks, Bernoulli cartridges, random access memories (RAMs), read only memories (ROMs), and the like, may be used in the exemplary operating environment. As is apparent to those of ordinary skill in the art, the hard disk drive 27 and other forms of computer-readable media (e.g., the removable magnetic disk 29, the removable optical disk 31, flash memory cards, SSD, USB drives, and the like) accessible by the processing unit 21 may be considered components of the system memory 22.

A number of program modules may be stored on the hard disk drive 27, magnetic disk 29, optical disk 31, ROM 24, or RAM 25, including the operating system 35, one or more application programs 36, other program modules 37, and program data 38. A user may enter commands and information into the computing device 12 through input devices such as a keyboard 40 and pointing device 42. Other input devices (not shown) may include a microphone, joystick, game pad, satellite dish, scanner, touch sensitive devices (e.g., a stylus or touch pad), video camera, depth camera, or the like. These and other input devices are often connected to the processing unit 21 through a serial port interface 46 that is coupled to the system bus 23, but may be connected by other interfaces, such as a parallel port, game port, a universal serial bus (USB), or a wireless interface (e.g., a Bluetooth interface). A monitor 47 or other type of display device is also connected to the system bus 23 via an interface, such as a video adapter 48. In addition to the monitor, computers typically include other peripheral output devices (not shown), such as speakers, printers, and haptic devices that provide tactile and/or other types of physical feedback (e.g., a force feedback game controller).

The input devices described above are operable to receive user input and selections. Together the input and display devices may be described as providing a user interface. The user interface may be configured to display various screens and dashboards and receive input entered into any of such screens.

The computing device 12 may operate in a networked environment using logical connections to one or more remote computers, such as remote computer 49. These logical connections are achieved by a communication device coupled to or a part of the computing device 12 (as the local computer).

Implementations are not limited to a particular type of communications device. The remote computer 49 may be another computer, a server, a router, a network PC, a client, a memory storage device, a peer device or other common network node, and typically includes many or all of the elements described above relative to the computing device 12. The remote computer 49 may be connected to a memory storage device 50. The logical connections depicted in FIG. 28 include a local-area network (LAN) 51 and a wide-area network (WAN) 52. Such networking environments are commonplace in offices, enterprise-wide computer networks, intranets and the Internet. The network may be implemented using one or more of the LAN 51 or the WAN 52 (e.g., the Internet).

Those of ordinary skill in the art will appreciate that a LAN may be connected to a WAN via a modem using a carrier signal over a telephone network, cable network, cellular network, or power lines. Such a modem may be connected to the computing device 12 by a network interface (e.g., a serial or other type of port). Further, many laptop computers may connect to a network via a cellular data modem.

When used in a LAN-networking environment, the computing device 12 is connected to the LAN 51 through a network interface or adapter 53, which is one type of communications device. When used in a WAN-networking environment, the computing device 12 typically includes a modem 54, a type of communications device, or any other type of communications device for establishing communications over the wide area network 52, such as the Internet. The modem 54, which may be internal or external, is connected to the system bus 23 via the serial port interface 46. In a networked environment, program modules depicted relative to the personal computing device 12, or portions thereof, may be stored in the remote computer 49 and/or the remote memory storage device 50. It is appreciated that the network connections shown are exemplary and other means of and communications devices for establishing a communications link between the computers may be used.

The computing device 12 and related components have been presented herein by way of particular example and also by abstraction in order to facilitate a high-level view of the concepts disclosed. The actual technical design and implementation may vary based on particular implementation while maintaining the overall nature of the concepts disclosed.

In some embodiments, the system memory 22 stores computer executable instructions (e.g., for all or portions of ocular distortion measurement method(s)) that when executed by one or more processors cause the one or more processors to perform all or portions of the method as described above. The system memory 22 may also store the dataset(s). Such instructions and/or dataset(s) may be stored on one or more non-transitory computer-readable or processor readable media.

Mobile Communication Device

Figure 29:
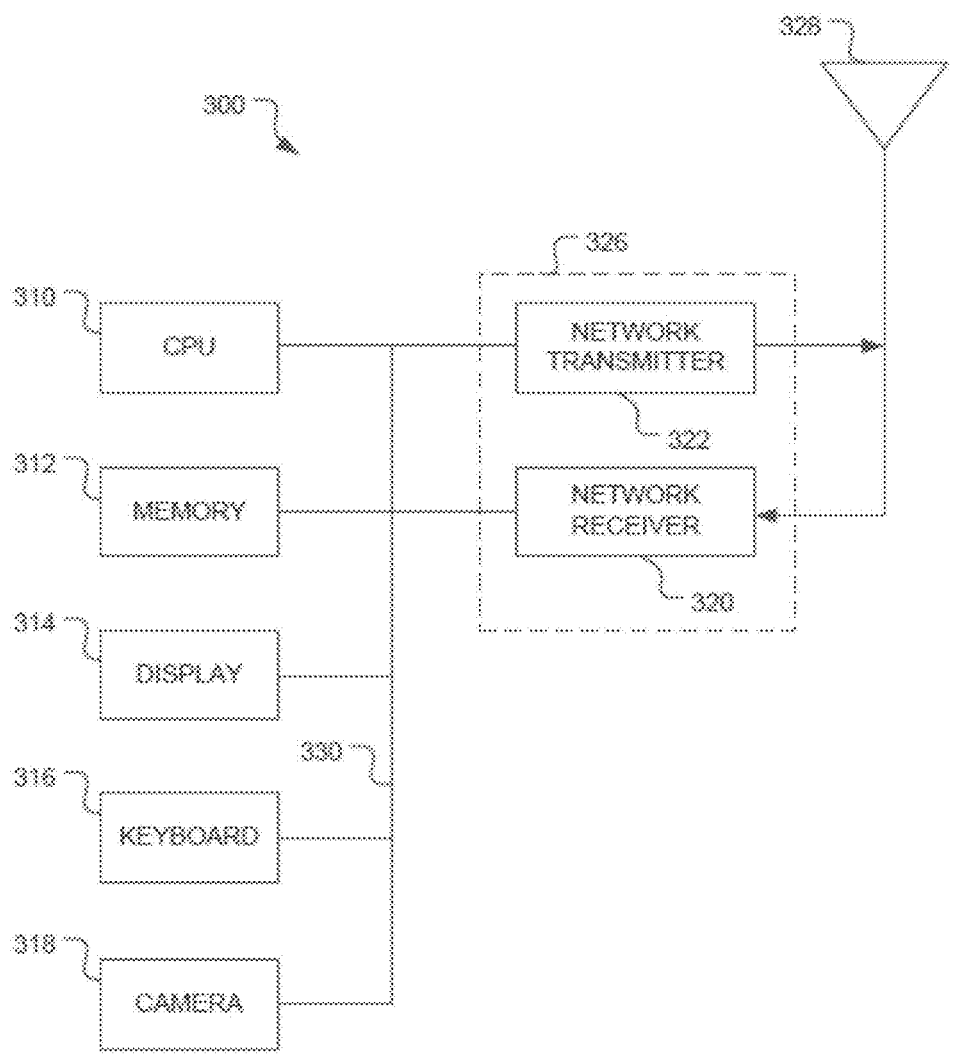
FIG. 29 shows an exemplary block diagram illustrating a mobile communication device 300 that may be used to implement one or more of the computing devices of the system.

FIG. 29 is a functional block diagram illustrating the mobile communication device 300 that may be used to implement one or more of the computing devices of the system. The mobile communication device 300 may be implemented as a cellular telephone, smart phone, a tablet computing device, and the like. By way of a non-limiting example, the mobile communication device 300 may be implemented as a smartphone executing IOS or Android OS.

The mobile communication device 300 includes a central processing unit ("CPU") 310. Those skilled in the art will appreciate that the CPU 310 may be implemented as a conventional microprocessor, application specific integrated circuit (ASIC), digital signal processor (DSP), programmable gate array (PGA), or the like. The mobile communication device 300 is not limited by the specific form of the CPU 310.

The mobile communication device 300 also contains the memory 312. The memory 312 may store instructions and data to control operation of the CPU 310. The memory 312 may include random access memory, ready-only memory, programmable memory, flash memory, and the like. The mobile communication device 300 is not limited by any specific form of hardware used to implement the memory 312. The memory 312 may also be integrally formed in whole or in part with the CPU 310.

The mobile communication device 300 also includes conventional components, such as a display 314, a keypad or keyboard 316, and a camera or video capture device 318. For example, the display 314 may be implemented as conventional touch screen display. These are conventional components that operate in a known manner and need not be described in greater detail. Other conventional components found in wireless communication devices, such as USB interface, Bluetooth interface, infrared device, and the like, may also be included in the mobile communication device 300. For the sake of clarity, these conventional elements are not illustrated in the functional block diagram of FIG. 29.

The display 314, the keyboard 316, and the camera or video capture device 318 are operable to receive user input and selections. Together the input and display devices may be described as providing a user interface. The user interface is configured to display the various screens and dashboards described above and receive input entered into any of these screens.

The mobile communication device 300 also includes a network transmitter 322 such as may be used by the mobile communication device 300 for normal network wireless communication with a base station (not shown). FIG. 8 also illustrates a network receiver 320 that operates in conjunction with the network transmitter 322 to communicate with the base station (not shown). In a typical embodiment, the network transmitter 322 and network receiver 320 are implemented as a network transceiver 326. The network transceiver 326 is connected to an antenna 328. Operation of the network transceiver 326 and the antenna 328 for communication with a wireless network (not shown) is well-known in the art and need not be described in greater detail herein.

The mobile communication device 300 may also include a conventional geolocation module (not shown) operable to determine the current location of the mobile communication device 300.

The various components illustrated in FIG. 29 are coupled together by the bus system 330. The bus system 330 may include an address bus, data bus, power bus, control bus, and the like. For the sake of convenience, the various busses in FIG. 8 are illustrated as the bus system 330.

The memory 312 may store instructions for the ocular distortion measurement method(s) executable by the CPU 310. When executed by the CPU 310, the instructions may cause the CPU 310 to perform to perform all or portions of the method(s) as described above. The memory 312 (see FIG. 8) may also store the dataset(s). Such instructions and/or dataset(s) may be stored on one or more non-transitory computer or processor readable media.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

References, incorporated herein by reference in their entirety for their respective relevant teachings:

1. F. DR, "Myopia," *Bmj*, vol. 324, no. May, pp. 1195-1199, 2002.
2. I. G. Morgan, K. Ohno-Matsui, and S.-M. Saw, "Myopia," in *The Lancet*, vol. 379, 2012, pp. 1739-1748.
3. L. L. K. Lin, Y. F. Shih, C. K. Hsiao, and C. J. Chen, "Prevalence of Myopia in Taiwanese Schoolchildren: 1983 to 2000," *Ann. Acad. Med. Singapore*, vol. 33, no. 1, pp. 27-33, 2004.
4. I. G. Morgan, K. A. Rose, L. B. Ellwein, and the R. E. S. in C. S. Refractive Error Study in Children Survey Group, "Is emmetropia the natural endpoint for human refractive development? An analysis of population-based data from the refractive error study in children (RESC)," *Acta Ophthalmol.*, vol. 88, no. 8, pp. 877-84, December 2010.
5. S. Vitale, R. D. Sperduto, and F. L. Ferris, "Increased Prevalence of Myopia in the United States Between 1971-1972 and 1999-2004," *Arch. Ophthalmol.*, vol. 127, no. 12, p. 1632, December 2009.
6. S.-M. Saw, G. Gazzard, E. C. Shih-Yen, and W.-H. Chua, "Myopia and associated pathological complications," *Ophthalmic Physiol. Opt.*, vol. 25, no. 5, pp. 381-391, September 2005.
7. F. Schaeffel and M. Feldkaemper, "Animal models in myopia research," *Clin. Exp. Optom.*, vol. 98, no. 6, pp. 507-517, 2015.
8. J. Wallman, J. Turkel, and J. Trachtman, "Extreme myopia produced by modest change in early visual experience", *Science*, vol. 201, no. 4362, pp. 1249-51, September 1978.
9. S. M. Sherman, T. T. Norton, and V. A. Casagrande, "Myopia in the lid-sutured tree shrew (*Tupaia glis*).," *Brain Res.*, vol. 124, no. 1, pp. 154-7, March 1977.
10. D. Trolio, D. L. Nickla, and C. F. Wildsoet, "Investigative ophthalmology & visual science.," *Invest. Ophthalmol. Vis. Sci.*, vol. 41, no. 8, pp. 2043-2049, July 2000.
11. E. Raviola and T. N. Wiesel, "Effect of dark-rearing on experimental myopia in monkeys.," *Invest. Ophthalmol. Vis. Sci.*, vol. 17, no. 6, pp. 485-8, June 1978.
12. F. Schaeffel, A. Glasser, and H. C. Howland, "Accommodation, refractive error and eye growth in chickens.," *Vision Res.*, vol. 28, no. 5, pp. 639-57, 1988.
13. A. W. Shaikh, J. T. Siegwart, and T. T. Norton, "Effect of interrupted lens wear on compensation for a minus lens in tree shrews.," *Optom. Vis. Sci.*, vol. 76, no. 5, pp. 308-15, May 1999.
14. B. Graham and S. J. Judge, "Normal development of refractive state and ocular component dimensions in the marmoset (*Callithrix jacchus*).," *Vision Res.*, vol. 39, no. 2, pp. 177-87, January 1999.
15. L. F. Hung, M. L. Crawford, and E. L. Smith, "Spectacle lenses alter eye growth and the refractive status of young monkeys.," *Nat. Med.*, vol. 1, no. 8, pp. 761-5, August 1995.
16. J. Wallman, M. D. Gottlieb, V. Rajaram, and L. A. Fugate-Wentzek, "Local retinal regions control local eye growth and myopia.," *Science*, vol. 237, no. 4810, pp. 73-7, July 1987.
17. Norton, T T and J. S, "Local myopia produced by partial visual field deprivation in tree shrew," *Soc. Neurosci. Abstr.*, vol. 17, p. 577, 1991.
18. A. Benavente-Perez, A. Nour, and D. Troilo, "Axial Eye Growth and Refractive Error Development Can Be Modified by Exposing the Peripheral Retina to Relative Myopic or Hyperopic Defocus," *Invest. Ophthalmol. Vis. Sci.*, vol. 55, no. 10, pp. 6765-6773, October 2014.
19. E. L. Smith, L.-F. Hung, J. Huang, and J. Huang, "Relative peripheral hyperopic defocus alters central refractive development in infant monkeys.," *Vision Res.*, vol. 49, no. 19, pp. 2386-92, September 2009.
20. D. Troilo, M. D. Gottlieb, and J. Wallman, "Visual deprivation causes myopia in chicks with optic nerve section," *Curr. Eye Res.*, vol. 6, no. 8, pp. 993-999, January 1987.
21. T. T. Norton, J. A. Essinger, and N. A. McBrien, "Lid-suture myopia in tree shrews with retinal ganglion cell blockade.," *Vis. Neurosci.*, vol. 11, no. 1, pp. 143-53, 1994.
22. L. He, M. R. Frost, and T. T. Norton, "Differential gene expression in tree shrew retina compared with retinal pigment epithelium (RPE) in response to six hours of minus-lens wear," *Invest. Ophthalmol. Vis. Sci.*, vol. 55, no. 13, pp. 3037-3037, April 2014.
23. X. Zhong, J. Ge, E. L. Smith, and W. K. Stell, "Image defocus modulates activity of bipolar and amacrine cells in macaque retina.," *Invest. Ophthalmol. Vis. Sci.*, vol. 45, no. 7, pp. 2065-74, July 2004.
24. R. A. Stone, T. Lin, A. M. Laties, and P. M. Iuvone, "Retinal dopamine and form-deprivation myopia.," *Proc. Natl. Acad. Sci. U.S.A.*, vol. 86, no. 2, pp. 704-6, January 1989.
25. N. A. McBrien, L. M. Cornell, and A. Gentle, "Structural and ultrastructural changes to the sclera in a mammalian model of high myopia.," *Invest. Ophthalmol. Vis. Sci.*, vol. 42, no. 10, pp. 2179-87, September 2001.
26. P. M. Iuvone, M. Tigges, R. A. Stone, S. Lambert, and A. M. Laties, "Effects of apomorphine, a dopamine receptor agonist, on ocular refraction and axial elongation in a primate model of myopia.," *Invest. Ophthalmol. Vis. Sci.*, vol. 32, no. 5, pp. 1674-7, April 1991.
27. M. FELDKAEMPER, S. DIETHER, G. KLEINE, and F. SCHAEFFEL, "Interactions of Spatial and Luminance Information in the Retina of Chickens During Myopia Development," *Exp. Eye Res.*, vol. 68, no. 1, pp. 105-115, January 1999.
28. A. J. Fischer, J. J. McGuire, F. Schaeffel, and W. K. Stell, "Light- and focus-dependent expression of the transcription factor ZENK in the chick retina," *Nat. Neurosci.*, vol. 2, no. 8, pp. 706-712, August 1999.
29. J. Winawer and J. Wallman, "Temporal constraints on lens compensation in chicks.," *Vision Res.*, vol. 42, no. 24, pp. 2651-68, November 2002.
30. E. L. Smith et al., "Effects of Foveal Ablation on Emmetropization and Form-Deprivation Myopia," *Investig. Opthalmology Vis. Sci.*, vol. 48, no. 9, p. 3914, September 2007.
31. R. Ashby, A. Ohlendorf, and F. Schaeffel, "The Effect of Ambient Illuminance on the Development of Deprivation Myopia in Chicks," *Investig. Opthalmology Vis. Sci.*, vol. 50, no. 11, p. 5348, November 2009.
32. R. S. Ashby and F. Schaeffel, "The Effect of Bright Light on Lens Compensation in Chicks," *Investig. Opthalmology Vis. Sci.*, vol. 51, no. 10, p. 5247, October 2010.
33. J. T. Siegwart, Jr., A. H. Ward, and T. T. Norton, "Moderately Elevated Fluorescent Light Levels Slow Form Deprivation and Minus Lens-Induced Myopia Development in Tree Shrews," *Invest. Ophthalmol. Vis. Sci.*, vol. 53, no. 14, pp. 3457-3457, March 2012.
34. T. T. Norton and J. T. Siegwart, "Light levels, refractive development, and myopia—A speculative review," *Exp. Eye Res.*, vol. 114, pp. 48-57, September 2013.
35. E. L. Smith, L.-F. Hung, B. Arumugam, J. Huang, and J. Huang, "Negative lens-induced myopia in infant mon- 35. keys: effects of high ambient lighting.," *Invest. Ophthalmol. Vis. Sci.*, vol. 54, no. 4, pp. 2959-69, April 2013.
36. E. L. Smith, L.-F. Hung, and J. Huang, "Protective Effects of High Ambient Lighting on the Development of Form-Deprivation Myopia in Rhesus Monkeys," *Investig. Opthalmology Vis. Sci.*, vol. 53, no. 1, p. 421, January 2012.
37. D. O. Mutti et al., "Corneal and Crystalline Lens Dimensions Before and After Myopia Onset," *Optom. Vis. Sci.*, vol. 89, no. 3, pp. 251-262, March 2012.
38. T. Y. P. Chui, D. Bissig, B. A. Berkowitz, and J. D. Akula, "Refractive Development in the "ROP Rat".," *J. Ophthalmol.*, vol. 2012, p. 956705, 2012.
39. D. I. Flitcroft, "The complex interactions of retinal, optical and environmental factors in myopia aetiology," *Prog. Retin. Eye Res.*, vol. 31, no. 6, pp. 622-660, 2012.
40. E. L. Smith, C. Kee, R. Ramamirtham, Y. Qiao-Grider, and L.-F. Hung, "Peripheral Vision Can Influence Eye Growth and Refractive Development in Infant Monkeys," *Investig. Opthalmology Vis. Sci.*, vol. 46, no. 11, p. 3965, November 2005.
41. J. Wallman and J. Winawer, "Homeostasis of Eye Growth and the Question of Myopia," *Neuron*, vol. 43, no. 4, pp. 447-468, August 2004.
42. D. O. Mutti, R. I. Sholtz, N. E. Friedman, and K. Zadnik, "Peripheral Refraction and Ocular Shape in Children," *Invest. Ophthalmol. Vis. Sci.*, vol. 41, no. 5, pp. 1022-1030, April 2000.
43. D. A. Atchison et al., "Eye Shape in Emmetropia and Myopia," *Investig. Opthalmology Vis. Sci.*, vol. 45, no. 10, p. 3380, October 2004.
44. D. A. Atchison, N. Pritchard, K. L. Schmid, D. H. Scott, C. E. Jones, and J. M. Pope, "Shape of the retinal surface in emmetropia and myopia," *Investig. Ophthalmol. Vis. Sci.*, vol. 46, no. 8, pp. 2698-2707, 2005.
45. J. Gwiazda, F. Thorn, J. Bauer, and R. Held, "Myopic children show insufficient accommodative response to blur," *Invest. Ophthalmol. Vis. Sci.*, vol. 34, no. 3, pp. 690-694, March 1993.
46. J. Gwiazda, J. Bauer, F. Thorn, and R. Held, "A dynamic relationship between myopia and blur-driven accommodation in school-aged children," *Vision Res.*, vol. 35, no. 9, pp. 1299-1304, May 1995.
47. D. O. Mutti et al., "The response AC/A ratio before and after the onset of myopia," *Investig. Ophthalmol. Vis. Sci.*, vol. 58, no. 3, pp. 1594-1602, 2017.
48. D. O. Mutti et al., "Refractive Error, Axial Length, and Relative Peripheral Refractive Error before and after the Onset of Myopia," *Investig. Opthalmology Vis. Sci.*, vol. 48, no. 6, p. 2510, June 2007.
49. D. O. Mutti et al., "Accommodative lag before and after the onset of myopia," *Investig. Ophthalmol. Vis. Sci.*, vol. 47, no. 3, pp. 837-846, 2006.
50. L. A. Jones-Jordan et al., "Early childhood refractive error and parental history of myopia as predictors of myopia.," *Invest. Ophthalmol. Vis. Sci.*, vol. 51, no. 1, pp. 115-21, January 2010.
51. I. Morgan and K. Rose, "How genetic is school myopia?," *Prog. Retin. Eye Res.*, vol. 24, no. 1, pp. 1-38, January 2005.
52. R. Pacella, J. McLellan, K. Grice, E. A. Del Bono, J. L. Wiggs, and J. E. Gwiazda, "Role of genetic factors in the etiology of juvenile-onset myopia based on a longitudinal study of refractive error.," *Optom. Vis. Sci.*, vol. 76, no. 6, pp. 381-6, June 1999.
53. R. Chakraborty, L. A. Ostrin, D. L. Nickla, P. M. Iuvone, M. T. Pardue, and R. A. Stone, "Circadian rhythms, refractive development, and myopia," *Ophthalmic Physiol. Opt.*, vol. 38, no. 3, pp. 217-245, 2018.
54. P. Kang et al., "Peripheral refraction in different ethnicities," *Investig. Ophthalmol. Vis. Sci.*, vol. 51, no. 11, pp. 6059-6065, 2010.
55. S. A. Read, M. J. Collins, and B. P. Sander, "Human Optical Axial Length and Defocus," *Investig. Opthalmology Vis. Sci.*, vol. 51, no. 12, p. 6262, December 2010.
56. J. Wallman et al., "Moving the retina: choroidal modulation of refractive state.," *Vision Res.*, vol. 35, no. 1, pp. 37-50, January 1995.
57. B. P. Sander, M. J. Collins, and S. A. Read, "The interaction between homatropine and optical blur on choroidal thickness," *Ophthalmic Physiol. Opt.*, vol. 38, no. 3, pp. 257-265, 2018.
58. X. Zhu, T. W. Park, J. Winawer, and J. Wallman, "In a Matter of Minutes, the Eye Can Know Which Way to Grow," *Investig. Opthalmology Vis. Sci.*, vol. 46, no. 7, p. 2238, July 2005.
59. D. Carlson, "Anatomy of the Human Eye—Infographic." [Online]. Available: https://owlcation.com/stem/Anatomy-of-the-Eye-Human-Eye-Anatomy. [Accessed: 30 May 2018].
60. A. J. Fischer, P. Miethke, I. G. Morgan, and W. K. Stell, "Cholinergic amacrine cells are not required for the progression and atropine-mediated suppression of form-deprivation myopia.," *Brain Res.*, vol. 794, no. 1, pp. 48-60, May 1998.
61. G. J. Lind, S. J. Chew, D. Marzani, and J. Wallman, "Muscarinic acetylcholine receptor antagonists inhibit chick scleral chondrocytes.," *Invest. Ophthalmol. Vis. Sci.*, vol. 39, no. 12, pp. 2217-31, November 1998.
62. W. A. Luft, Y. Ming, and W. K. Stell, "Variable effects of previously untested muscarinic receptor antagonists on experimental myopia.," *Invest. Ophthalmol. Vis. Sci.*, vol. 44, no. 3, pp. 1330-8, March 2003.
63. N. A. McBrien, H. O. Moghaddam, and A. P. Reeder, "Atropine reduces experimental myopia and eye enlargement via a nonaccommodative mechanism.," *Invest. Ophthalmol. Vis. Sci.*, vol. 34, no. 1, pp. 205-15, January 1993.
64. L. B. Wilson et al., "The Relation of Axial Length and Intraocular Pressure Fluctuations in Human Eyes," *Investig. Opthalmology Vis. Sci.*, vol. 47, no. 5, p. 1778, May 2006.
65. R. Chakraborty, S. A. Read, and M. J. Collins, "Diurnal Variations in Axial Length, Choroidal Thickness, Intraocular Pressure, and Ocular Biometrics," Investig. *Opthalmology Vis. Sci.*, vol. 52, no. 8, p. 5121, July 2011.
66. R. B. Rabbetts, *Bennett & Rabbetts' clinical visual optics*. Elsevier/Butterworth Heinemann, 2007.
67. S. Weiss and F. Schaeffel, "Diurnal growth rhythms in the chicken eye: relation to myopia development and retinal dopamine levels.," *J. Comp. Physiol. A.*, vol. 172, no. 3, pp. 263-70, April 1993.
68. D. L. Nickla and K. Totonelly, "Brief light exposure at night disrupts the circadian rhythms in eye growth and choroidal thickness in chicks," *Exp. Eye Res.*, vol. 146, pp. 189-195, May 2016.
69. D. L. Nickla, K. Jordan, J. Yang, and K. Totonelly, "Brief hyperopic defocus or form deprivation have varying effects on eye growth and ocular rhythms depending on the time-of-day of exposure," *Exp. Eye Res.*, vol. 161, pp. 132-142, August 2017.
70. K. S. Korshunov, L. J. Blakemore, and P. Q. Trombley, "Dopamine: A Modulator of Circadian Rhythms in the Central Nervous System," *Front. Cell. Neurosci.*, vol. 11, p. 91, April 2017.

71. C. R. Jackson et al., "Retinal Dopamine Mediates Multiple Dimensions of Light-Adapted Vision," *J. Neurosci.*, vol. 32, no. 27, pp. 9359-9368, July 2012.

72. C. Ribelayga and S. C. Mangel, "Absence of circadian clock regulation of horizontal cell gap junctional coupling reveals two dopamine systems in the goldfish retina," *J. Comp. Neurol.*, vol. 467, no. 2, pp. 243-253, December 2003.

73. B. Rohrer, P. M. Iuvone, and W. K. Stell, "Stimulation of dopaminergic amacrine cells by stroboscopic illumination or fibroblast growth factor (bFGF, FGF-2) injections: possible roles in prevention of form-deprivation myopia in the chick.," *Brain Res.*, vol. 686, no. 2, pp. 169-81, July 1995.

74. J. Liang, B. Grimm, S. Goelz, and J. F. Bille, "Objective measurement of wave aberrations of the human eye with the use of a Hartmann-Shack wave-front sensor.," *J. Opt. Soc. Am. A. Opt. Image Sci. Vis.*, vol. 11, no. 7, pp. 1949-1957, July 1994.

75. X. Cheng, A. Bradley, X. Hong, N. Thibos, and Larry N, "Relationship between Refractive Error and Monochromatic Aber . . . : Optometry and Vision Science," *Optom. Vis. Sci.*, vol. 80, no. 1, pp. 43-49, 2003.

76. L. Llorente, S. Barbero, D. Cano, C. Dorronsoro, and S. Marcos, "Myopic versus hyperopic eyes: axial length, corneal shape and optical aberrations," *J. Vis.*, vol. 4, no. 4, p. 5, 2004.

77. S. Marcos, S. A. Burns, P. M. Prieto, R. Navarro, and B. Baraibar, "Investigating sources of variability of monochromatic and transverse chromatic aberrations across eyes," *Vision Res.*, vol. 41, no. 28, pp. 3861-3871, 2001.

78. W. N. Charman, "Aberrations and myopia," *Ophthalmic Physiol. Opt.*, vol. 25, no. 4, pp. 285-301, July 2005.

79. A. Mathur, D. A. Atchison, and W. N. Charman, "Myopia and peripheral ocular aberrations," *J. Vis.*, vol. 9, no. 10, pp. 15-15, September 2009.

80. A. Hartwig and D. A. Atchison, "Analysis of Higher-Order Aberrations in a Large Clinical Population," *Investig. Opthalmology Vis. Sci.*, vol. 53, no. 12, p. 7862, November 2012.

81. T. Buehren, M. J. Collins, D. R. Iskander, B. Davis, and B. Lingelbach, "The stability of corneal topography in the post-blink interval.," *Cornea*, vol. 20, no. 8, pp. 826-33, November 2001.

82. P. Kang, "Optical and pharmacological strategies of myopia control," *Clin. Exp. Optom.*, vol. 101, no. 3, pp. 321-332, 2018.

83. J. J. Walline, K. Lindsley, S. S. Vedula, S. A. Cotter, D. O. Mutti, and J. D. Twelker, "Interventions to slow progression of myopia in children," *Cochrane Database Syst. Rev.*, no. 12, p. CD004916, December 2011.

84. J. Katz et al., "A randomized trial of rigid gas permeable contact lenses to reduce progression of children's myopia.," *Am. J. Ophthalmol.*, vol. 136, no. 1, pp. 82-90, July 2003.

85. J. J. Walline, L. A. Jones, D. O. Mutti, and K. Zadnik, "A Randomized Trial of the Effects of Rigid Contact Lenses on MyopiaProgression," *Arch. Ophthalmol.*, vol. 122, no. 12, p. 1760, December 2004.

86. K. Chung, N. Mohidin, and D. J. O'Leary, "Undercorrection of myopia enhances rather than inhibits myopia progression.," *Vision Res.*, vol. 42, no. 22, pp. 2555-9, October 2002.

87. S.-M. Li et al., "Studies using concentric ring bifocal and peripheral add multifocal contact lenses to slow myopia progression in school-aged children: a meta-analysis," *Ophthalmic Physiol. Opt.*, vol. 37, no. 1, pp. 51-59, January 2017.

88. S. Barbero and M. Faria-Ribeiro, "Foveal vision power errors induced by spectacle lenses designed to correct peripheral refractive errors," *Ophthalmic Physiol. Opt.*, vol. 38, no. 3, pp. 317-325, 2018.

89. D. Cheng, G. C. Woo, and K. L. Schmid, "Bifocal lens control of myopic progression in children," *Clin. Exp. Optom.*, vol. 94, no. 1, pp. 24-32, January 2011.

90. J. Gwiazda et al., "A randomized clinical trial of progressive addition lenses versus single vision lenses on the progression of myopia in children.," *Invest. Ophthalmol. Vis. Sci.*, vol. 44, no. 4, pp. 1492-500, April 2003.

91. D. Cheng, K. L. Schmid, and G. C. Woo, "The effect of positive-lens addition and base-in prism on accommodation accuracy and near horizontal phoria in Chinese myopic children," *Ophthalmic Physiol. Opt.*, vol. 28, no. 3, pp. 225-237, April 2008.

92. Correction of Myopia Evaluation Trial 2 Study Group for the Pediatric Eye Disease Investigator Group, "Progressive-Addition Lenses versus Single-Vision Lenses for Slowing Progression of Myopia in Children with High Accommodative Lag and Near Esophoria," *Invest. Ophthalmol. Vis. Sci.*, vol. 52, no. 5, pp. 2749-2757, April 2011.

93. G. W. Fulk, L. A. Cyert, and D. E. Parker, "A randomized trial of the effect of single-vision vs. bifocal lenses on myopia progression in children with esophoria.," *Optom. Vis. Sci.*, vol. 77, no. 8, pp. 395-401, August 2000.

94. O. Pärssinen, E. Hemminki, and A. Klemetti, "Effect of spectacle use and accommodation on myopic progression: final results of a three-year randomised clinical trial among schoolchildren.," *Br. J. Ophthalmol.*, vol. 73, no. 7, pp. 547-51, July 1989.

95. G. W. Fulk and L. A. Cyert, "Can bifocals slow myopia progression?," *J. Am. Optom. Assoc.*, vol. 67, no. 12, pp. 749-54, December 1996.

96. T. Grosvenor, D. M. Perrigin, J. Perrigin, and B. Maslovitz, "Houston Myopia Control Study: a randomized clinical trial. Part II. Final report by the patient care team.," *Am. J. Optom. Physiol. Opt.*, vol. 64, no. 7, pp. 482-98, July 1987.

97. D. Cheng, G. C. Woo, B. Drobe, and K. L. Schmid, "Effect of Bifocal and Prismatic Bifocal Spectacles on Myopia Progression in Children," *JAMA Ophthalmol.*, vol. 132, no. 3, p. 258, March 2014.

98. T. Uemura, Y. Arai, and C. Shimazaki, "Eye-Head Coordination During Lateral Gaze in Normal Subjects," *Acta Otolaryngol.*, vol. 90, no. 1-6, pp. 191-198, January 1980.

99. T. Schilling, A. Ohlendorf, S. R. Varnas, and S. Wahl, "Peripheral Design of Progressive Addition Lenses and the Lag of Accommodation in Myopes," *Investig. Opthalmology Vis. Sci.*, vol. 58, no. 9, p. 3319, July 2017.

100. T. A. Aller, M. Liu, and C. F. Wildsoet, "Myopia Control with Bifocal Contact Lenses," *Optom. Vis. Sci.*, vol. 93, no. 4, pp. 344-352, 2016.

101. P. Sankaridurg et al., "Spectacle Lenses Designed to Reduce Progression of Myopia: 12-Month Results," *Optom. Vis. Sci.*, vol. 87, no. 9, pp. 631-641, September 2010.

102. J. J. Walline, K. L. Greiner, M. E. McVey, and L. A. Jones-Jordan, "Multifocal contact lens myopia control," *Optom. Vis. Sci.*, vol. 90, no. 11, pp. 1207-1214 en 2013.

103. P. Sankaridurg et al., "Decrease in Rate of Myopia Progression with a Contact Lens Designed to Reduce Relative Peripheral Hyperopia: One-Year Results," *Investig. Opthalmology Vis. Sci.*, vol. 52, no. 13, p. 9362, December 2011.

104. C. S. Y. Lam, W. C. Tang, D. Y. Y. Tse, Y. Y. Tang, and C. H. To, "Defocus Incorporated Soft Contact (DISC) lens slows myopia progression in Hong Kong Chinese schoolchildren: A 2-year randomised clinical trial," *Br. J. Ophthalmol.*, vol. 98, no. 1, pp. 40-45, 2014.

105. J. Pauné, H. Morales, J. Armengol, L. Quevedo, M. Faria-Ribeiro, and J. M. Gonzelez-Méijome, "Myopia Control with a Novel Peripheral Gradient Soft Lens and Orthokeratology: A 2-Year Clinical Trial," *Biomed Res. Int.*, vol. 2015, no. D, 2015.

106. J. Pauné, A. Queiros, D. Lopes-Ferreira, M. Faria-Ribeiro, L. Quevedo, and J. M. Gonzalez-Meijome, "Efficacy of a Gas Permeable Contact Lens to Induce Peripheral Myopic Defocus," *Optom. Vis. Sci.*, vol. 92, no. 5, pp. 596-603, May 2015.

107. J. Pauné, A. Queiros, L. Quevedo, H. Neves, D. Lopes-Ferreira, and J. M. González-Méijome, "Peripheral myopization and visual performance with experimental rigid gas permeable and soft contact lens design," *Contact Lens Anterior Eye*, vol. 37, no. 6, pp. 455-460, December 2014.

108. N. S. Anstice and J. R. Phillips, "Effect of dual-focus soft contact lens wear on axial myopia progression in children," *Ophthalmology*, vol. 118, no. 6, pp. 1152-1161, 2011.

109. B. N. Cheng X, Xu J, Chehab K, Exford J, "Soft Contact Lenses with Positive Spherical," vol. 93, no. 4, pp. 353-366, 2016.

110. E. L. Smith, "Optical treatment strategies to slow myopia progression: Effects of the visual extent of the optical treatment zone," *Exp. Eye Res.*, vol. 114, pp. 77-88, September 2013.

111. P. Gifford and K. L. Gifford, "The future of myopia control contact lenses," *Optom. Vis. Sci.*, vol. 93, no. 4, pp. 336-343, 2016.

112. P. Kang, Y. Fan, K. Oh, K. Trac, F. Zhang, and H. A. Swarbrick, "The effect of multifocal soft contact lenses on peripheral refraction," *Optom. Vis. Sci.*, vol. 90, no. 7, pp. 658-666, 2013.

113. D. A. Berntsen and C. E. Kramer, "Peripheral Defocus with Spherical and Multifocal Soft Contact Lenses," *Optom. Vis. Sci.*, vol. 90, no. 11, pp. 1215-1224, November 2013.

114. D. Lopes-Ferreira et al., "Peripheral myopization using a dominant design multifocal contact lens," *J. Optom.*, vol. 4, no. 1, pp. 14-21, January 2011.

115. J. Huang et al., "Efficacy comparison of 16 interventions for myopia control in children: A network meta-analysis," *Ophthalmology*, vol. 123, no. 4, pp. 697-708, 2016.

116. Y. Sun et al., "Orthokeratology to Control Myopia Progression: A Meta-Analysis," *PLoS One*, vol. 10, no. 4, p. e0124535, April 2015.

117. J.-K. Si, K. Tang, H.-S. Bi, D.-D. Guo, J.-G. Guo, and X.-R. Wang, "Orthokeratology for Myopia Control," *Optom. Vis. Sci.*, vol. 92, no. 3, pp. 252-257, March 2015.

118. T. Hiraoka, Y. Sekine, F. Okamoto, T. Mihashi, and T. Oshika, "Safety and efficacy following 10-years of overnight orthokeratology for myopia control," *Ophthalmic Physiol. Opt.*, vol. 38, no. 3, pp. 281-289, 2018.

119. P. Cho and S. W. Cheung, "Discontinuation of orthokeratology on eyeball elongation (DOEE)," *Contact Lens Anterior Eye*, vol. 40, no. 2, pp. 82-87, April 2017.

120. D. Chen, A. K. C. Lam, and P. Cho, "Posterior corneal curvature change and recovery after 6 months of overnight orthokeratology treatment," *Ophthalmic Physiol. Opt.*, vol. 30, no. 3, pp. 274-280, May 2010.

121. A. Mathur and D. A. Atchison, "Effect of Orthokeratology on Peripheral Aberrations of the Eye," *Optom. Vis. Sci.*, vol. 86, no. 5, pp. E476-E484, May 2009.

122. P. Ganesan and C. F. Wildsoet, "Pharmaceutical intervention for myopia control.," *Expert Rev. Ophthalmol.*, vol. 5, no. 6, pp. 759-787, December 2010.

123. F. Schaeffel, D. Troilo, J. Wallman, and H. C. Howland, "Developing eyes that lack accommodation grow to compensate for imposed defocus.," *Vis. Neurosci.*, vol. 4, no. 2, pp. 177-83, February 1990.

124. C. L. Cottriall and N. A. McBrien, "The M1 muscarinic antagonist pirenzepine reduces myopia and eye enlargement in the tree shrew.," *Invest. Ophthalmol. Vis. Sci.*, vol. 37, no. 7, pp. 1368-79, June 1996.

125. R. M. Siatkowski et al., "Safety and Efficacy of 2% Pirenzepine Ophthalmic Gel in Children WithMyopia," *Arch. Ophthalmol.*, vol. 122, no. 11, p. 1667, November 2004.

126. W. H. Chua et al., "Atropine for the Treatment of Childhood Myopia," *Ophthalmology*, vol. 113, no. 12, pp. 2285-2291, 2006.

127. A. Chia et al., "Atropine for the treatment of childhood Myopia: Safety and efficacy of 0.5%, 0.1%, and 0.01% doses (Atropine for the Treatment of Myopia 2)," *Ophthalmology*, vol. 119, no. 2, pp. 347-354, 2012.

128. A. Chia, W. H. Chua, L. Wen, A. Fong, Y. Y. Goon, and D. Tan, "Atropine for the treatment of childhood myopia: Changes after stopping atropine 0.01%, 0.1% and 0.5%," *Am. J. Ophthalmol.*, vol. 157, no. 2, p. 451-457.e1, 2014.

129. L. Tong, X. L. Huang, A. L. T. Koh, X. Zhang, D. T. H. Tan, and W. H. Chua, "Atropine for the Treatment of Childhood Myopia: Effect on Myopia Progression after Cessation of Atropine," *Ophthalmology*, vol. 116, no. 3, pp. 572-579, 2009.

130. E. H. Leung and R. Rosen, "Atlas of Wide-Field Retinal Angiography and Imaging," pp. 1-25, 2016.

131. H. Littmann, "Die Zeiss Funduskamera," in *59th Meeting of German Ophthalmology*, 1955.

132. E. DeHoog and J. Schwiegerling, "Fundus camera systems: a comparative analysis.," *Appl. Opt.*, vol. 48, no. 2, pp. 221-228, 2009.

133. O. Pomerantzeff, R. H. Webb, and F. C. Delori, "Image formation in fundus cameras," *Investig. Ophthalmol. Vis. Sci.*, vol. 18, no. 6, pp. 630-637, 1979.

134. M. Hammer, A. Roggan, D. Schweitzer, and G. Muller, "Optical properties of ocular fundus tissues—an in vitro study using the double-integrating-sphere technique and inverse Monte Carlo simulation," *Phys. Med. Biol.*, vol. 40, no. 6, pp. 963-978, June 1995.

135. N. P. A. Zagers, J. van de Kraats, T. T. J. M. Berendschot, and D. van Norren, "Simultaneous measurement of foveal spectral reflectance and cone-photoreceptor directionality," *Appl. Opt.*, vol. 41, no. 22, p. 4686, August 2002.

136. B. BENGTSSON and C. E. T. KRAKAU, "Some Essential Optical Features of the Zeiss Fundus Camera," *Acta Ophthalmol.*, vol. 55, no. 1, pp. 123-131, 1977.

137. W. Smith, *Modern Optical Engineering—Chapter 3—Abberations*, Third. SPIE, 2000.

138. R. Barakat and A. Houston, "The Aberrations of Non-Rotationally Symmetric Systems and Their Diffraction Effects," vol. 13, no. 1, pp. 1-30, 1966.

139. R. Navarro, "The optical design of the human eye: A critical review," *J. Optom.*, vol. 2, no. 1, pp. 3-18, 2009.
140. J. Schwiegerling, "Arizona Eye Model," in *Field Guide to Visual and Ophthalmic Optics*, SPIE, 2004.
141. D. A. Atchison and G. Smith, *Optics of the human eye*. Butterworth-Heinemann, 2000.
142. J. Porter, A. Guirao, I. G. Cox, and D. R. Williams, "Monochromatic aberrations of the human eye in a large population.," *J. Opt. Soc. Am. A. Opt. Image Sci. Vis.*, vol. 18, no. 8, pp. 1793-803, August 2001.
143. J. J. Rozema, D. A. Atchison, and M. J. Tassignon, "Statistical eye model for normal eyes," *Investig. Ophthalmol. Vis. Sci.*, vol. 52, no. 7, pp. 4525-4533, 2011.
144. J. Schwiegerling, "Statistical generation of normal and post-refractive surgery wavefronts," *Clin. Exp. Optom.*, vol. 92, no. 3, pp. 223-226, 2009.
145. D. A. Atchison, E. L. Markwell, S. Kasthurirangan, J. M. Pope, G. Smith, and P. G. Swann, "Age-related changes in optical and biometric characteristics of emmetropic eyes," *J. Vis.*, vol. 8, no. 4, p. 29, April 2008.
146. J. E. Greivenkamp, *Field guide to geometricaloptics*. SPIE Press, 2004.
147. J. Varikooty, N. Keir, C. A. Woods, and D. Fonn, "Measurement of the refractive index of soft contact lenses during wear," *Eye Contact Lens*, vol. 36, no. 1, pp. 2-5, 2010.
148. E. Kim, R. C. Bakaraju, and K. Ehrmann, "Power Profiles of Commercial Multifocal Soft Contact Lenses," *Optom. Vis. Sci.*, vol. 94, no. 2, pp. 183-196, 2017.
149. J. Nam, L. N. Thibos, and D. R. Iskander, "Describing ocular aberrations with wavefront vergence maps," *Clin. Exp. Optom.*, vol. 92, no. 3, pp. 194-205, 2009.
150. M. Rodriguez-Vallejo, J. Benlloch, A. Pons, J. A. Monsoriu, and W. D. Furlan, "The effect of fractal contact lenses on peripheral refraction in myopic model eyes," *Curr. Eye Res.*, vol. 39, no. 12, pp. 1151-1160, 2014.
[151] J. Sasian, "Introduction to Aberrations & Geometrical-Optics Based Imaging—Lecture 15—Pupil Aberrations." pp. 1-27.

What is claimed is:

1. A method for measuring ocular distortion present in an eye of a subject, comprising:
    illuminating a known target pattern having characteristic features and positioned in a plane of an illumination path of a retinal imaging system that is conjugate to a retinal plane;
    projecting an image of the target pattern onto an area of the retinal plane to provide a distorted retinal image of the target pattern across the area of the retinal surface;
    projecting the distorted retinal image of the target pattern to an image sensor positioned in an imaging path of the retinal imaging system, wherein the retinal image of the target pattern is passed through a lens configuration to correct for any ametropia of the eye to correct for subject astigmatism;
    recording the distorted retinal image of the target pattern using the image sensor to provide a captured distorted retinal image of the target pattern across the area of the retinal surface;
    identifying the characteristic features of the captured distorted retinal image of the target pattern across the area of the retinal surface; and
    comparing the identified characteristic features of the captured distorted retinal image of the target pattern across the area of the retinal surface to corresponding characteristic features of the known target pattern to provide a map of ocular distortion across the area of the retinal surface, wherein the preceding steps are applied to the subject over time to monitor or track temporal changes or progression in the distortion relative to a distortion metric to provide a method for detecting early onset myopia or hyperopia.

2. The method of claim 1, comprising quantifying the amount of ocular distortion and/or determining the type of ocular distortion.

3. The method of claim 1, wherein the retinal imaging system comprises a fundus camera configured to include the known target pattern having the characteristic features and positioned in the plane of the illumination path of the fundus camera that is conjugate to a retinal plane.

4. The method of claim 1, wherein the target pattern comprises fiducials suitable for quantifying ocular distortion, the pattern being one or more selected from the amplitude pattern group consisting of a rectilinear grid pattern, concentric ring pattern, and variable density grid pattern, or from the phase pattern group consisting of a phase plate, diffractive optic, and null correcting plate.

5. The method of claim 1, wherein the target pattern is a phase target pattern placed in the illumination path of the retinal imaging system at a location that is a Fourier transform plane of the retina, the phase target having a suitable pattern such that its Fourier transform creates a suitable amplitude pattern on the retina for measuring ocular distortion.

6. The method of claim 5, wherein the amplitude pattern comprises one or more of a grid pattern, concentric circles, or arrays of dots.

7. The method of claim 1, wherein identifying the characteristic features of the captured distorted retinal image of the target pattern across the area of the retinal surface, comprises use of frequency space image processing to automatically detect centroid signatures from the target pattern.

8. The method of claim 7, wherein a variable frequency pass method is swept across the image to remove intensity variations, and suppress strong optic disc and blood vessel objects while boosting the distorted target pattern to the foreground.

9. The method of claim 8, wherein centroid or corner detection is completed to identify various grid positions across the retinal surface.

10. The method of claim 2, wherein quantifying the amount of ocular distortion and/or determining the type of ocular distortion comprises using mathematical fitting.

11. The method of claim 10, comprising correlating, using a mathematical fitting algorithm, the distorted retinal image of the target pattern across the area of the retinal surface, with the known grid pattern, free from distortion, across the area of the retinal surface.

12. The method of claim 11, comprising calibration of the retinal imaging system for inherent distortion to provide for an absolute measurement of ocular distortion.

13. The method of claim 1, wherein the retinal imaging system is configured to distinguish between distortion caused by retinal imaging system misalignment and local changes in retinal topography, to provide for extracting a diagnostic of global and local retinal curvature.

14. The method of claim 1, further comprising repetition of the method steps across one or more additional areas of the retinal surface to provide a map of ocular distortion across a larger retinal area, preferably comprising use of a stitching algorithm.

15. The method of claim 14, comprising combining eye rotation and continuous distortion mapping.

16. The method of claim 1, further comprising use of suitable real-time image processing software to examine blood vessel features in the retinal image to provide autofocus of the image and to ensure alignment of the eye between consecutive images.

17. The method of claim 16, wherein the retinal imaging system and software are configured to track the human eye and gaze direction ensuring eye alignment, to provide useful information on eye orientation during distortion measurement.

18. The method of claim 1, applied during critical years of eye growth.

19. The method of claim 1, further comprising implementing corrective or control measures for ocular distortion selected from the group consisting of spectacle lenses, contact lenses, multifocal lenses, and combinations thereof.

20. A system for measuring ocular distortion present in an eye, comprising:
  a retinal imaging system comprising an illumination system having an illumination source and an illumination path, and an imaging system having an image sensor and an imaging path, wherein the illumination path is configured to project light from the illumination source to a retinal plane of a subject eye to illuminate a retinal surface area, and wherein the imaging path is configured for projecting scattered light emerging from the illuminated retinal surface area to the image sensor, wherein the imaging path comprises a lens configuration to correct for any ametropia of the eye to correct for subject astigmatism;
  a known target pattern having characteristic features positioned and configured in a plane of the illumination path that is conjugate to the retinal plane, such that upon illumination an image of the known target pattern is projectable onto the retinal surface area to provide for a distorted retinal image of the target pattern across the area of the retinal surface, and wherein the image sensor is configured for recording of the distorted retinal image of the target pattern across the area of the retinal surface; and
  wherein the configuration of the illumination path prevents simultaneous viewing of another object that is outside the imaging system, such that the shape of the imaged pattern is not subject to variable accommodation by the subject eye.

21. The system of claim 20, further comprising computer-implemented software for identifying the characteristic features of the captured distorted retinal image of the target pattern across the area of the retinal surface, and comparing the identified characteristic features of the captured distorted retinal image of the target pattern across the area of the retinal surface to corresponding characteristic features of the known target pattern to provide a map of ocular distortion across the area of the retinal surface.

22. The system of claim 20, further comprising computer-implemented software for real-time image processing of blood vessel features in the retinal image to provide for autofocus of the image and for eye alignment between consecutive images.

23. The system of claim 22, wherein the retinal imaging system and software are configured to track the eye and gaze direction to provide for eye alignment, to provide useful information on eye orientation during distortion measurement.

24. The system of claim 20, wherein the target pattern comprises fiducials suitable for quantifying ocular distortion, the pattern being one or more selected from the amplitude pattern group consisting of a rectilinear grid pattern, concentric ring pattern, and variable density grid pattern, or from the phase pattern group consisting of a phase plate, diffractive optic, and null correcting plate.

25. The system of claim 20, wherein the target pattern is a phase target pattern placed in the illumination path of the retinal imaging system at a location that is a Fourier transform plane of the retina, the phase target having a suitable pattern such that its Fourier transform creates a suitable amplitude pattern on the retina for measuring ocular distortion.

26. The system of claim 24, wherein the amplitude pattern comprises one or more of a grid pattern, concentric circles, or arrays of dots.

27. The system of claim 20, wherein the retinal imaging system comprises a fundus camera.

* * * * *